(12) United States Patent
Masuda et al.

(10) Patent No.: US 9,536,480 B2
(45) Date of Patent: Jan. 3, 2017

(54) IMAGE DISPLAY DEVICE AND CONTROL METHOD THEREOF

(71) Applicant: CANON KABUSHIKI KAISHA, Tokyo (JP)

(72) Inventors: Chika Masuda, Sagamihara (JP); Yuka Fujinaka, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/449,301

(22) Filed: Aug. 1, 2014

(65) Prior Publication Data

US 2015/0042583 A1 Feb. 12, 2015

(30) Foreign Application Priority Data

Aug. 6, 2013 (JP) .................................. 2013-163511

(51) Int. Cl.
*G09G 5/10* (2006.01)
*G09G 3/34* (2006.01)
(Continued)

(52) U.S. Cl.
CPC ............. *G09G 3/3426* (2013.01); *A61B 6/463* (2013.01); *G02B 27/023* (2013.01); *G06F 3/0412* (2013.01); *G06F 3/14* (2013.01); *G09G 3/001* (2013.01); *G09G 3/3611* (2013.01); *G09G 2300/023* (2013.01); *G09G 2310/0232* (2013.01); *G09G 2310/04* (2013.01); *G09G 2320/0686* (2013.01); *G09G 2340/0464* (2013.01); *G09G 2370/022* (2013.01); *G09G 2370/04* (2013.01); *G09G 2380/08* (2013.01)

(58) Field of Classification Search
USPC ............. 345/87, 173, 690, 694, 84, 60, 639; 435/119
See application file for complete search history.

(56) References Cited

U.S. PATENT DOCUMENTS

| | | | | |
|---|---|---|---|---|
| 2001/0011976 A1* | 8/2001 | Kasahara | ............. | G09G 3/2022 345/60 |
| 2001/0029038 A1* | 10/2001 | Summer | .............. | C07D 503/00 435/119 |

(Continued)

FOREIGN PATENT DOCUMENTS

| | | |
|---|---|---|
| DE | 19948621 A1 | 4/2001 |
| JP | 07-275209 A | 10/1995 |
| JP | 2001-235704 A | 8/2001 |

OTHER PUBLICATIONS

The above references were cited in a Great Britain Search Report issued on Feb. 6, 2015, that issued in the corresponding Great Britain Patent Application No. GB1413860.6.

*Primary Examiner* — Thuy Pardo
(74) *Attorney, Agent, or Firm* — Cowan, Liebowitz & Latman, P.C.

(57) ABSTRACT

An image display device including: a light-emitting unit that is capable of individually controlling emission amounts in each of a plurality of regions constituting a screen; a display unit that displays an image on the screen; and a control unit that sets a first region in which display is performed at a predetermined brightness and a second region in which an image is displayed at a lower brightness than the predetermined brightness in the screen, wherein the control unit sets the second region in a region excluding the first region in the screen on the basis of an influence of light leakage from the first region.

30 Claims, 25 Drawing Sheets

(51) Int. Cl.
*G06F 3/041* (2006.01)
*G06F 3/14* (2006.01)
*G09G 3/00* (2006.01)
*G09G 3/36* (2006.01)
*A61B 6/00* (2006.01)
*G02B 27/02* (2006.01)

(56) References Cited

U.S. PATENT DOCUMENTS

| | | | |
|---|---|---|---|
| 2002/0036650 A1* | 3/2002 | Kasahara | G09G 3/2022 345/639 |
| 2005/0104896 A1 | 5/2005 | Kerr et al. | |
| 2008/0018575 A1* | 1/2008 | Kobayashi | G02B 6/0076 345/87 |
| 2008/0136846 A1* | 6/2008 | Abe | G09G 3/3685 345/690 |
| 2011/0050760 A1* | 3/2011 | Ito | G09G 3/3426 345/694 |
| 2011/0115829 A1* | 5/2011 | Ito | G09G 3/3426 345/690 |
| 2011/0292097 A1* | 12/2011 | Kobayashi | G02F 1/1336 345/690 |
| 2012/0086738 A1* | 4/2012 | Shimizu | G09G 3/3426 345/690 |
| 2012/0313983 A1* | 12/2012 | Sasaki | G09G 3/2092 345/690 |

* cited by examiner

| DIFFERENCE IN BRIGHTNESS [cd/m²] | LIGHT LEAKAGE INFLUENCE DISTANCE [pixel] |
|---|---|
| 500 | 200 |
| 600 | 210 |
| 700 | 220 |
| ⋮ | ⋮ |
| 1500 | 300 |
| ⋮ | ⋮ |

*Fig.8*

DISPLAY IMAGE

SCREEN AS SEEN FROM USER

CENTER OF GRAVITY POINT OF FILM PLACEMENT REGION

CENTER OF GRAVITY POINTS OF DIGITAL IMAGES

DISTANCES BETWEEN CENTER OF GRAVITY POINTS

DISPLAY IMAGE

SCREEN AS SEEN FROM USER

IMAGE DISPLAY DEVICE AND CONTROL METHOD THEREOF

BACKGROUND OF THE INVENTION

Field of the Invention

The present invention relates to an image display device and a control method thereof.

Description of the Related Art

In recent years, progress has been made in the digitalization of image diagnostic devices (hereinafter, referred to as modalities) as represented by an X-ray imaging device, an ultrasonic diagnostic device, and a magnetic resonance imaging device. As a result, more and more images captured by a modality are being managed as medical images outputted as digital data (digital images) instead of medical images outputted as film (film images).

However, since we are still in a transitional period between managing images as film images and managing images as digital images, images are being managed in a state where film images and digital images coexist. A comparative diagnosis of an old image managed as a film image and a current image managed as a digital image requires performing a comparison by placing the film image on an x-ray film illuminator and displaying the digital image on an image display device (medical monitor). In such a combinatorial state, since the x-ray film illuminator and the medical monitor which are installed at different locations must be alternately viewed, a diagnostician's line of sight movement increases and diagnostic efficiency declines.

In order to solve this problem, medical image diagnosis supporting devices (for example, refer to Japanese Patent Application Laid-open No. H7-275209) are proposed in which a panel is installed on a part of an x-ray film illuminator and which enable a film image and a digital image to be observed simultaneously.

In addition, medical image display devices (for example, refer to Japanese Patent Application Laid-open No. 2001-235704) are proposed which display a white image in a partial region of a screen of an image display device and which use the white image display region as an x-ray film illuminator to enable a film image and a digital image to be observed simultaneously in the screen of the image display device.

SUMMARY OF THE INVENTION

When a diagnostician comparatively diagnoses a film image and a digital image, a position where the film image is placed and a position where the digital image is displayed are desirably as close to each other as possible.

However, with the conventional art described above, a layout of a placement position of a film image and a display position of a digital image is not considered. Therefore, displaying a film image and a digital image next to each other in order to facilitate comparative diagnosis requires an operation by a diagnostician himself/herself involving moving the film image and/or the digital image so that the film image and the digital image become adjacent to each other. As a result, diagnostic efficiency declines.

Meanwhile, a liquid crystal display device is developed which is capable of performing control referred to as local dimming in which an emission brightness of a backlight is changed for each region.

With local dimming, a display region can be divided into an "x-ray film illuminator region" and a "second region". In this case, an x-ray film illuminator region refers to a region which emits light at high brightness and which is used as an x-ray film illuminator. A second region refers to a region which emits light at normal brightness and which is used to display a digital image. Accordingly, both a film image and a digital image can be observed by one liquid crystal display device.

However, a difference is created between the brightness of the x-ray film illuminator region (approximately, 2000 cd/m$^2$) and the brightness of the second region (approximately, 500 cd/m$^2$). Therefore, leakage of backlight light of an x-ray film illuminator region occurs in a second region that is positioned around the x-ray film illuminator region and may cause a decline in display image quality of a digital image.

The present invention automatically sets a first region or a second region so that display image quality of the second region is prevented from declining in an image display device capable of using a part of a screen as lighting when observing through an observation object.

A first aspect of the present invention is an image display device including:

a light-emitting unit that is capable of individually controlling emission amounts in each of a plurality of regions constituting a screen;

a display unit that displays an image on the screen; and a control unit that configured to set a first region in which display is performed at a predetermined brightness and a second region in which an image is displayed at a lower brightness than the predetermined brightness in the screen, wherein the control unit sets the second region in a region excluding the first region in the screen on the basis of an influence of light leakage from the first region.

A second aspect of the present invention is an image display device including:

a light-emitting unit that is capable of individually controlling emission amounts in each of a plurality of regions constituting a screen;

a display unit that displays an image on the screen; and a control unit configured to set a first region in which display is performed at a predetermined brightness and a second region in which an image is displayed at a lower brightness than the predetermined brightness in the screen, wherein the control unit sets the first region in a region excluding the second region in the screen on the basis of an influence of light leakage from the first region.

A third aspect of the present invention is a control method for an image display device including:

a light-emitting unit that is capable of individually controlling emission amounts in each of a plurality of regions constituting a screen; and a display unit that displays an image on the screen, the control method including:

individually controlling emission amounts in each of the plurality of regions; and implementing control of setting a first region in which display is performed at a predetermined brightness and a second region in which an image is displayed at a lower brightness than the predetermined brightness in the screen, wherein the control includes setting the second region in a region excluding the first region in the screen based on an influence of light leakage from the first region.

According to the present invention, an illuminated region or an image display region is automatically set so that display image quality in the image display region is prevented from declining in an image display device capable of using a part of a screen as lighting when observing through an observation object.

Further features of the present invention will become apparent from the following description of exemplary embodiments (with reference to the attached drawings).

BRIEF DESCRIPTION OF THE DRAWINGS

FIG. 8 is a diagram showing an example of a light leakage table according to the first embodiment;

DESCRIPTION OF THE EMBODIMENTS

Hereinafter, embodiments of an image display device and an image display system according to the present invention will be described.

First Embodiment

In the present embodiment, a comparative diagnosis system including an image display device capable of display by dividing a single screen into two regions including an x-ray film illuminator region (a first region) and an image display region (a second region) and one example of a control method for the comparative diagnosis system will be described. When a placement position of a film image is determined, the comparative diagnosis system according to the present embodiment determines an x-ray film illuminator region in accordance with the placement position of the film image. In addition, a digital image is automatically laid out and displayed at a position which is not influenced by light leakage from an x-ray film illuminator region (the influence is within a permissible level) and which is as close to the x-ray film illuminator region as possible.

Figure 2:
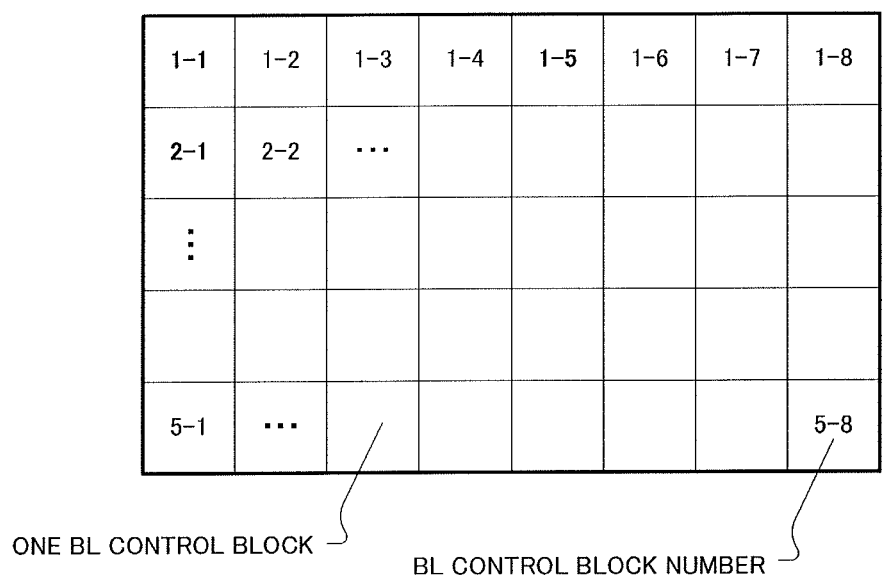
FIG. 2 is a diagram showing an example of an arrangement of BL control blocks according to the first embodiment.

Hereinafter, the present embodiment will be described with reference to the drawings. FIG. 2 shows an example of a configuration of a comparative diagnosis system to which the present invention is applied. The comparative diagnosis system is constituted by a liquid crystal display device 1 and a control device 2. The liquid crystal display device 1 and the control device 2 are connected to each other by two signal lines including an image signal line 3 and a communication signal line 4. In the present embodiment, a Digital Visual Interface (DVI) cable is used as the former and a Universal Serial Bus (USB) cable is used as the latter.

The liquid crystal display device 1 is a medical monitor equipped with a local dimming function that enables brightness to be locally controlled in a screen. During divided display that involves using the local dimming function to display an x-ray film illuminator region in which white display is performed at brightness for an x-ray film illuminator and an image display region in which an image is displayed at brightness for image display are arranged side by side, backlight brightness can be individually adjusted per region. An x-ray film illuminator region is an illuminated region in which display is performed at a predetermined brightness which assumes use as lighting when observing through an observation object such as a film image. A brightness for image display of an image display region is lower than the predetermined brightness of the x-ray film illuminator region. The liquid crystal display device 1 receives image data (image signal) outputted by the control device 2 (to be described later) through a DVI cable and displays the image data on a screen based on the image data. In addition, the liquid crystal display device 1 receives a control instruction from the control device 2 through a USB cable and performs an operation in accordance with the control instruction. While an example of a case where the display device is a transmissive liquid crystal display device will be described in the present embodiment, the display device is not limited to a transmissive liquid crystal display device. The display device need only be a display device that includes an independent light source. For example, the display device may be a reflective liquid crystal display device. In addition, the display device may be a micro electro mechanical system (MEMS) shutter system display that uses a MEMS shutter instead a liquid crystal element.

The control device 2 is a control device that controls the liquid crystal display device 1 that is a medical viewer for observing medical digital images. Software that runs on a personal computer (PC) or a control board that is built into the PC is assumed as the control device 2.

Figure 1:
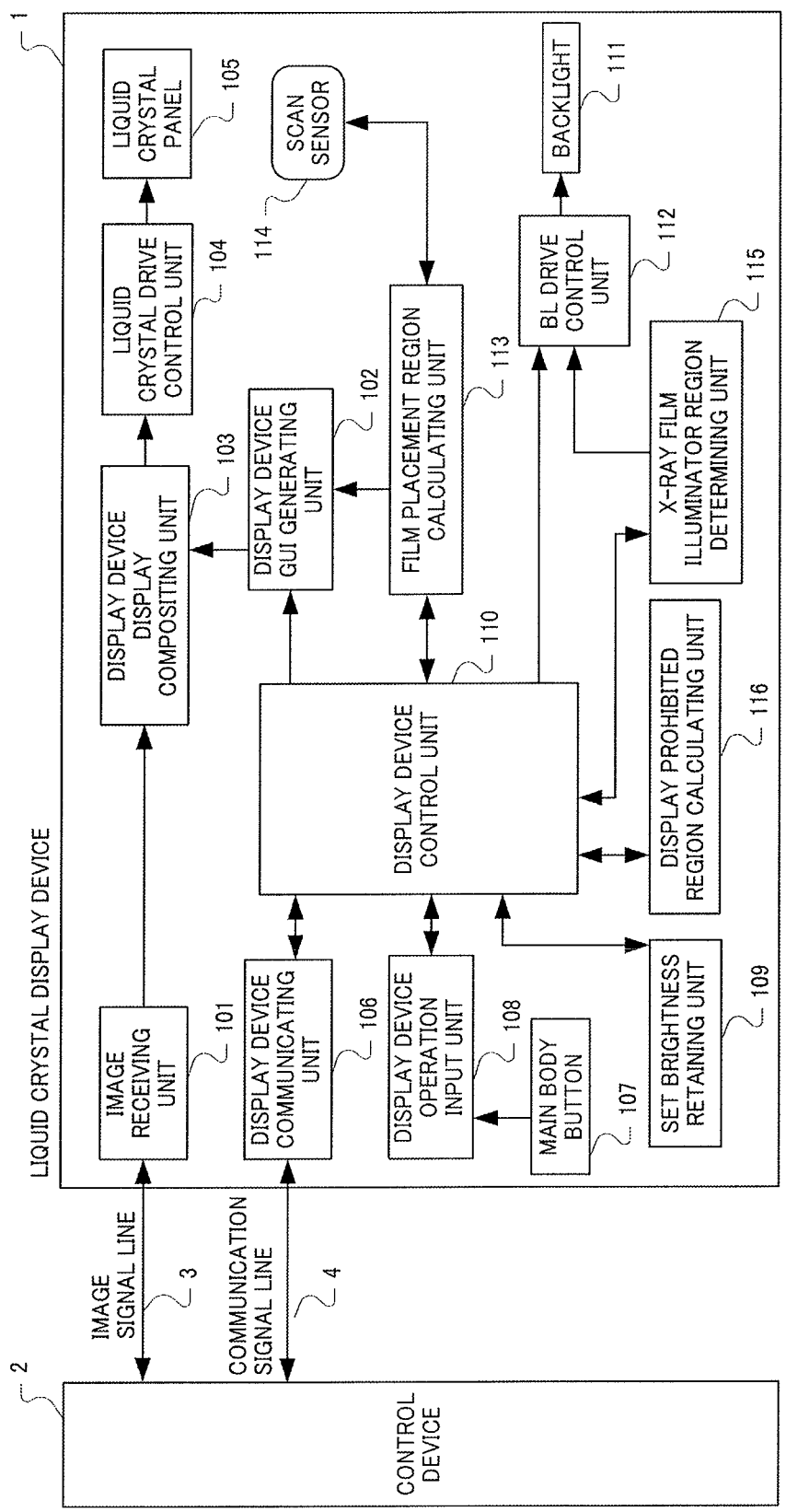
FIG. 1 is a block diagram showing a configuration of a liquid crystal display device according to a first embodiment.

Next, respective function blocks of the liquid crystal display device 1 will be described with reference to FIG. 1.

An image receiving unit 101 receives image data from the control device 2 via the image signal line 3 and transmits the image data to a display device display compositing unit 103 (to be described later).

A display device GUI generating unit 102 generates image data for displaying a graphical user interface (GUI) such as a warning and a message in response to an instruction from a display device control unit 110 (to be described later) and transmits the image data to the display device display compositing unit 103 (to be described later). In addition, the display device GUI generating unit 102 also receives an instruction to generate a white display patch for an x-ray film illuminator region from the display device control unit 110, creates a white display patch in an instructed size, and transmits the white display patch to the display device display compositing unit 103.

The display device display compositing unit 103 composites image data inputted from the image receiving unit 101 and image data for GUI display inputted from the display device GUI generating unit 102 and transmits the obtained image data to a liquid crystal drive control unit 104.

The liquid crystal drive control unit 104 converts the image data inputted from the display device display compositing unit 103 into a control signal for a liquid crystal panel 105 (to be described later) and transmits the image data to the liquid crystal panel 105 to perform display control of the liquid crystal panel 105.

The liquid crystal panel 105 receives the control signal from the liquid crystal drive control unit 104, and by driving liquid crystals according to the control signal, modulates light from a backlight 111 and displays an image on the panel.

A display device communicating unit 106 receives a communication command related to control of the liquid crystal display device 1 from the control device 2 via the communication signal line 4, analyzes contents of the command, and transmits an analysis result to the display device control unit 110 (to be described later). In addition, in accordance with a command transmission instruction from the display device control unit 110, the display device communicating unit 106 creates a communication command and transmits the communication command to the control device 2. Detailed contents of communication will be described in the flows presented below.

A main body button 107 is an operation button for accepting an operation by the user to input an instruction to the liquid crystal display device 1.

A display device operation input unit 108 recognizes a user operation performed using the main body button 107 and transmits operation contents to the display device control unit 110 (to be described later).

A set brightness retaining unit 109 is a memory (storage device) that retains a set brightness of an x-ray film illuminator region and a set brightness of an image display device. The set brightness of both regions can be changed by the user at will. Using the main body button 107, the user performs an operation for inputting a set brightness change instruction to the liquid crystal display device 1 via a dedicated GUI (not shown) for changing the set brightness. Contents of the user operation are interpreted by the display device control unit 110 and a set brightness corresponding to the contents of the user operation is written into the set brightness retaining unit 109. As a result, a changed set brightness is retained.

The display device control unit 110 performs control of the liquid crystal display device 1 in general such as a process for writing a set brightness changed by a user operation into the set brightness retaining unit 109 and a process for causing the display device GUI generating unit 102 to output image data for GUI display. In addition, the display device control unit 110 receives a control instruction received from the control device 2 from the display device communicating unit 106. Furthermore, in accordance with contents of the control instruction, the display device control unit 110 controls the display device GUI generating unit 102, a film placement region calculating unit 113, an x-ray film illuminator region determining unit 115, a display prohibited region calculating unit 116, and a BL drive control unit 112 (to be described later). Accordingly, a process for performing divided display of an x-ray film illuminator region and an image display region is performed. Detailed contents will be described in the flow titled <Divided display process> to be presented below.

The backlight 111 includes a plurality of light-emitting diodes (LED) as light sources in a matrix pattern and is installed in a rear part of the liquid crystal panel 105. As shown in FIG. 2, the backlight 111 is constituted by a plurality of divided regions (hereinafter, referred to as "BL control blocks", here, "BL" is an abbreviation for "backlight") that are capable of individually controlling brightness. Each divided region is assigned a unique number (hereinafter, referred to as a "BL control block number"). The backlight 111 is light-emitting means capable of individually controlling an emission amount in each of a plurality of regions that constitute the screen. Moreover, the light-emitting means is not limited to a backlight for a liquid crystal display device and may be any illumination device configured so as to be capable of individually controlling light irradiated to display means that displays an image for each region.

The BL drive control unit 112 performs a process for controlling emission brightness (emission amount) of each BL control block of the backlight 111 in accordance with an instruction from the display device control unit 110.

In accordance with an instruction from the display device control unit 110, the film placement region calculating unit 113 uses a scan sensor 114 (to be described later) to calculate a film placement region (position information of a region in which a film is placed) on the screen of the liquid crystal display device 1.

The scan sensor 114 is a driven two-dimensional image sensor installed on a front surface of the liquid crystal panel 105. Under control by the film placement region calculating unit 113, the scan sensor 114 scans the front surface of the liquid crystal panel 105 and creates a scanned image. When a film image is placed on the front surface of the liquid crystal panel 105 during execution of scanning by the scan sensor 114, a scanned image including the film image is created. By analyzing the scanned image including the film image, the film placement region calculating unit 113 is capable of detecting a placement position of the film image.

In accordance with an instruction from the display device control unit 110, the x-ray film illuminator region determining unit 115 determines a BL control block to be used as an x-ray film illuminator region and a region in the screen to be used as an x-ray film illuminator region.

In accordance with an instruction from the display device control unit 110, the display prohibited region calculating unit 116 calculates a "display prohibited region" in the screen of the liquid crystal display device 1 during divided display. In this case, a display prohibited region refers to a region in which a digital image to be used for a comparative diagnosis with a film image is not displayed when displaying the digital image next to an x-ray film illuminator region. The display prohibited region is a region combining a region in which a digital image cannot be displayed due to the region being an x-ray film illuminator region and a region in which a digital image is desirably not displayed because, for example, the appearance of colors changes due to the influence of light leakage from an x-ray film illuminator region.

While there are blocks other than those described above for executing basic functions as a liquid crystal display device, description of such blocks will be omitted herein.

Figure 3:
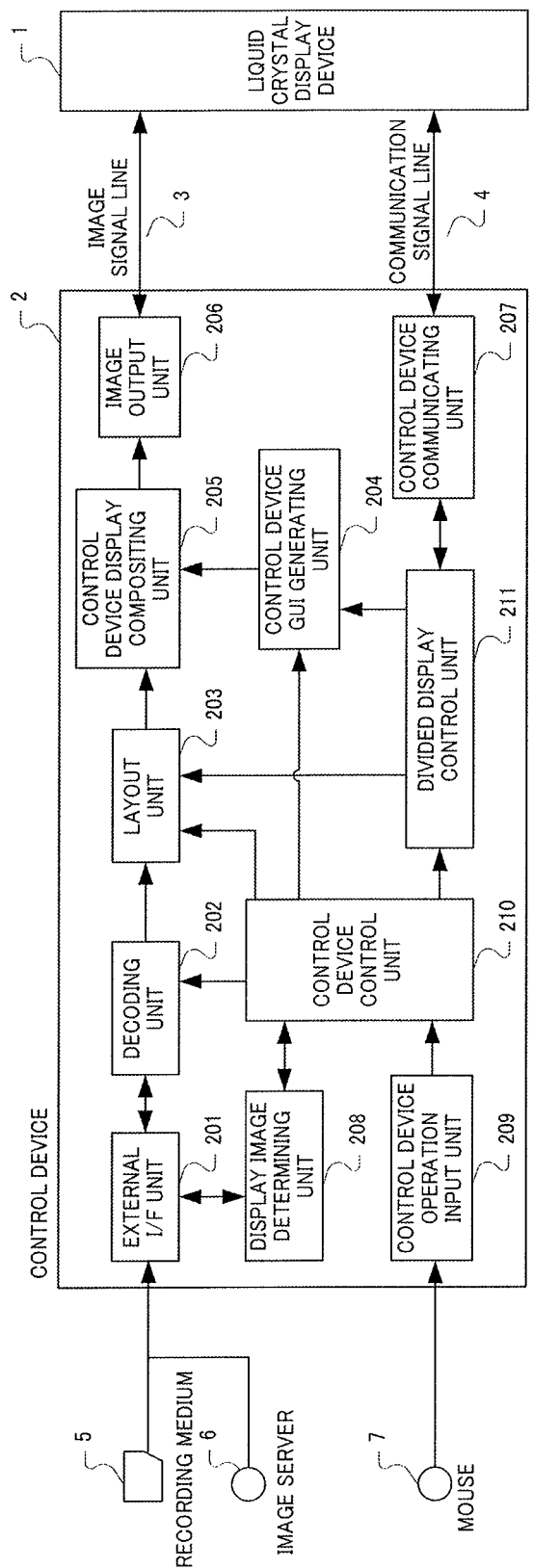
FIG. 3 is a block diagram showing a configuration of a control device according to the first embodiment.

Next, respective function blocks of the control device 2 will be described with reference to FIG. 3.

An external I/F unit 201 accesses an external recording medium 5 such as an SD memory card and an image server 6 for medical images. The image server 6 is an image server installed on a hospital network such as a picture archiving and communications system (PACS). In accordance with an instruction from a decoding unit 202 (to be described later), the external I/F unit 201 reads digital image data in the recording medium 5 or the image server 6.

The decoding unit 202 performs a decoding process on digital image data acquired via the external I/F unit 201 and transmits decoded image data to a layout unit 203 (to be described later).

The layout unit 203 receives a layout instruction from a control device control unit 210 or a divided display control unit 211 (to be described later) and performs a layout process on image data received from the decoding unit 202. In this case, contents of a layout instruction include designation of a position such as "center of screen" and designation of a display region (a horizontal coordinate x and a vertical coordinate y of an origin, a width w, and a height h) of image data in the screen. A layout process is a process of performing scaling and arrangement in order to display an image based on image data at a position or in a display region designated by a layout instruction.

A control device GUI generating unit 204 generates image data for displaying a GUI such as a warning and a message in response to an instruction from the control device control unit 210 and transmits the image data to a control device display compositing unit 205 (to be described later).

The control device display compositing unit 205 composites image data inputted from the layout unit 203 and image data for GUI display inputted from the control device GUI generating unit 204 and transmits the obtained image data to an image output unit 206.

The image output unit 206 transmits image data composited by the control device display compositing unit 205 to the liquid crystal display device 1 through the image signal line 3.

A control device communicating unit 207 creates a communication command in accordance with a command transmission instruction from a divided display control unit 211 (to be described later) and transmits the communication command to the liquid crystal display device 1. In addition, the control device communicating unit 207 receives a communication command from the liquid crystal display device 1, analyzes command contents, and transmits an analysis result to the divided display control unit 211. Detailed contents of communication will be described in the flows presented below.

A display image determining unit 208 receives an instruction from the control device control unit 210 (to be described later) and determines a digital image that is automatically displayed during divided display. A detail process will be described in the flow titled <Display digital image determination process> to be presented below.

A control device operation input unit 209 recognizes a user operation performed using a mouse 7 and transmits operation contents to the control device control unit 210 (to be described later).

By causing the decoding unit 202 to read and perform a decoding process on appropriate digital image data in accordance with a user operation, the control device control unit 210 causes a digital image designated by the user in the screen of the liquid crystal display device 1 and performs management of the digital image that is being displayed. In addition, by issuing an instruction for GUI display to the control device GUI generating unit 204, the control device control unit 210 causes the control device GUI generating unit 204 to create image data for GUI display that is necessary for control and display a GUI. Furthermore, after receiving an instruction to perform divided display of an x-ray film illuminator region and an image display device according to a user operation, the control device control unit 210 realizes divided display using the divided display control unit 211 (to be described later). Detailed contents of communication will be described in <Control process of control unit> presented below.

The divided display control unit 211 receives a divided display instruction from the control device control unit 210 and controls the control device GUI generating unit 204 and the liquid crystal display device 1 to perform a process for realizing divided display of an x-ray film illuminator region and an image display device. At this point, the divided display control unit 211 performs control so as to lay out and display a digital image at a position which is not influenced by light leakage from an x-ray film illuminator region and which is as close to the x-ray film illuminator region as possible. A detailed process will be described in the flow titled <Divided display process> to be presented below.

Next, a divided display process of the comparative diagnosis system according to the present embodiment will be described with reference to the flow charts shown in FIGS. 4A, 4B, and 5.

Figure 6A:
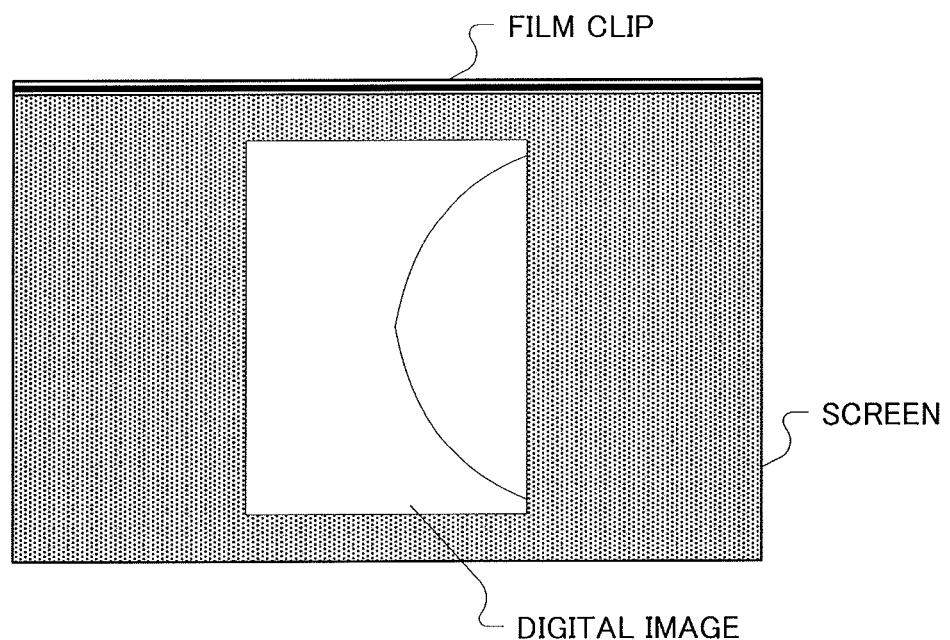
FIGS. 6A and 6B show a screen prior to divided display and an example of a GUI display that prompts placement of a film image according to the first embodiment.

As shown in FIG. 6A, let us assume that a medical digital image read from the recording medium 5 or the image server 6 is displayed in the screen of the liquid crystal display device 1 and is used for diagnosis prior to performing divided display. In the control device 2, the control device control unit 210 uses the decoding unit 202 to decode the digital image data acquired from the recording medium 5 or the image server 6 and issues a layout instruction to the layout unit 203 so that the digital image is to be displayed in an arbitrary size at "center of screen". The control device 2 creates image data (display data) for performing display such as that shown in FIG. 6A and outputs the image data to the liquid crystal display device 1. Accordingly, a digital image display state shown in FIG. 6A is realized.

A film clip for holding and fixing a film image such as that shown in FIG. 6A is provided in an upper part of the liquid crystal panel 105 of the liquid crystal display device 1 and is used when the user places the film image.

It is assumed that a timing at which the comparative diagnosis system starts divided display is a timing at which the control device 2 causes a GUI (not shown) for setting ON/OFF of divided display to be displayed and the user performs an operation to set divided display=ON on the GUI using the mouse 7.

<Control Process of Control Device Control Unit 210>

First, a process of the control device control unit 210 will be described using the flow chart shown in FIG. 4A.

Figures 4A, 4B:
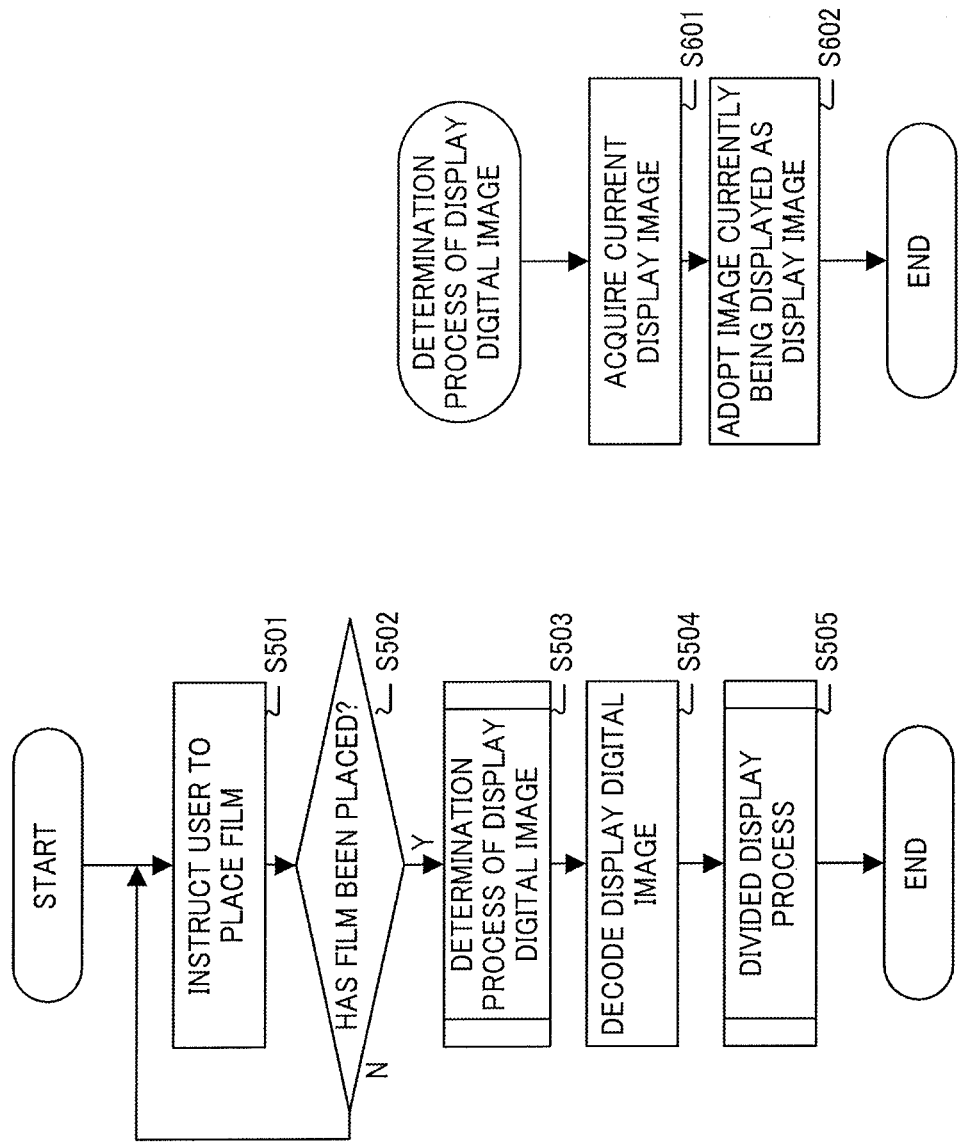
FIGS. 4A and 4B are flow charts representing dividing process control and a display digital image determining process according to the first embodiment.

It is assumed that the flow chart shown in FIG. 4A starts at a time point where, in a state in which only a digital image is displayed in the screen such as shown in FIG. 6A, the control device control unit 210 detects that divided display=ON has been set by a user operation using the mouse 7.

Figure 6B:
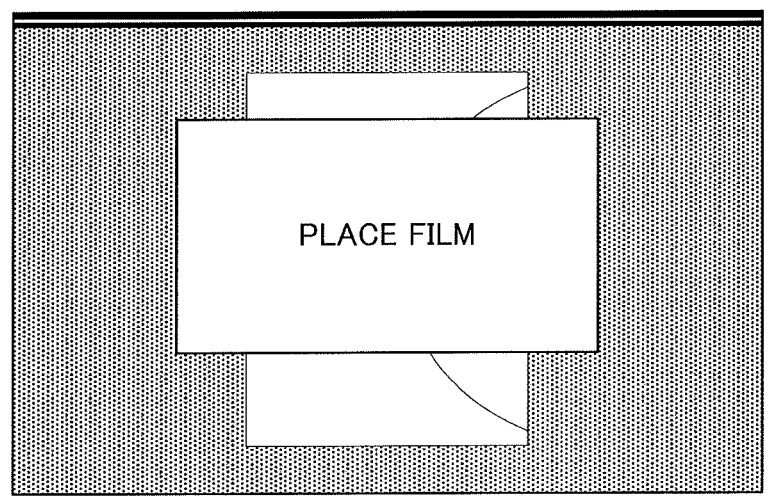

In step S501, the control device control unit 210 issues an instruction to the control device GUI generating unit 204 to generate a GUI for prompting placement of a film image. As a result of this process, a GUI such as that shown in FIG. 6B is displayed on the screen (the liquid crystal panel 105) of the liquid crystal display device 1.

In step S502, the control device control unit 210 determines whether or not the film image has been placed on the screen. In the present embodiment, this determination is made based on whether or not an operation (for example, a left click) has been performed by the user using the mouse 7 to input to the control device 2 completion of film placement during display of the GUI shown in FIG. 6B. When the operation has been performed, the control device control unit 210 determines that the film image has been placed and advances the process to step S503 after erasing the GUI. When the operation has not been performed, the control device control unit 210 determines that the film image has not been placed and returns the process to step S501.

In step S503, the control device control unit 210 issues an instruction to the display image determining unit 208 to determine a digital image to be displayed when performing divided display (hereinafter, referred to as a display digital image) and acquires a file path to the display digital image.

In step S504, the control device control unit 210 instructs the decoding unit 202 to read and decode image data at the file path of the display digital image acquired in step S503. Upon receiving the instruction, the decoding unit 202 reads and decodes the image data at the file path of the display digital image and transmits the decoded image data to the control device display compositing unit 205.

In step S505, the control device control unit 210 issues an instruction to the divided display control unit 211 to perform divided display and ends the process.

<Determination Process of Display Digital Image>

Next, a determination process performed by the display image determining unit 208 of a digital image (display digital image) to be automatically displayed during divided display will be described with reference to the flow chart shown in FIG. 4B. In the present embodiment, a digital image that is displayed when divided display=ON is set is determined as a display digital image.

The flow chart shown in FIG. 4B represents details of the process performed in step S503 in the flow chart shown in FIG. 4A. It is assumed that the flow chart shown in FIG. 4B is executed at a time point where the display image determining unit 208 receives a determination instruction of a display digital image from the control device control unit 210.

In step S601, the display image determining unit 208 acquires a file path of a digital image currently being displayed from the control device control unit 210.

In step S602, the display image determining unit 208 returns the file path acquired in step S601 to the control device control unit 210 and ends the process.

According to the process described above, a digital image that is being displayed at the moment where divided display=ON is set can be determined as a display digital image and a file path of the display digital image can be returned to the control device control unit 210.

<Divided Display Process>

Next, a divided display process will be described with reference to the flow chart shown in FIG. 5.

Figure 5:
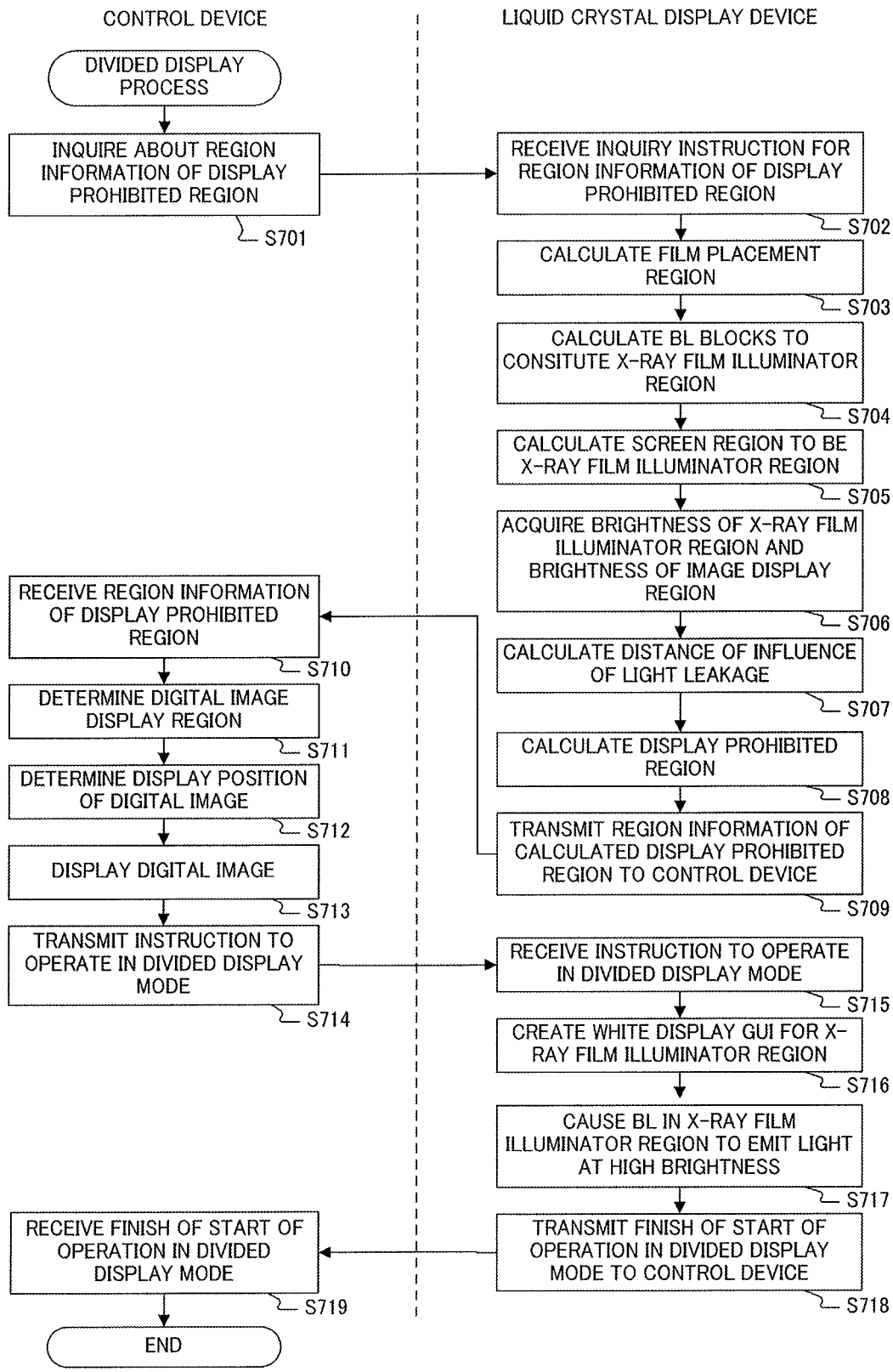
FIG. 5 is a flow chart showing a processing procedure of divided display according to the first embodiment.

The flow chart shown in FIG. 5 represents details of the process performed in step S505 in the flow chart shown in FIG. 4A. It is assumed that the flow chart shown in FIG. 5 is executed at a time point where the divided display control unit 211 of the control device 2 receives a divided display instruction from the control device control unit 210.

In step S701, the divided display control unit 211 of the control device 2 uses the control device communicating unit 207 to transmit a command for inquiring a display prohibited region of a digital image to the liquid crystal display device 1. A display prohibited region is a region that combines an x-ray film illuminator region with a region in which an image cannot be accurately displayed due to light leakage from the x-ray film illuminator region.

In step S702, the display device communicating unit 106 of the liquid crystal display device 1 receives the command and notifies the command to the display device control unit 110.

In step S703, the display device control unit 110 of the liquid crystal display device 1 receives an inquiry instruction with respect to a display prohibited region from the display device communicating unit 106 and first issues an instruction to the film placement region calculating unit 113 to calculate a film placement region.

Figure 7A:
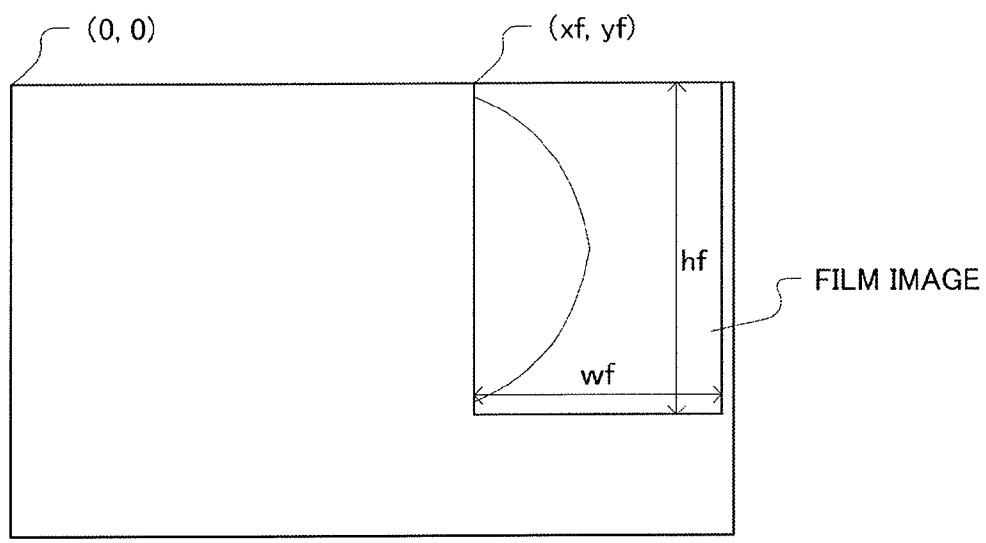
FIGS. 7A and 7B show examples of a scanned image and an x-ray film illuminator region BL control block according to the first embodiment.

Upon receiving the instruction from the display device control unit 110, the film placement region calculating unit 113 of the liquid crystal display device 1 instructs the display device GUI generating unit 102 to create a white display patch to be displayed on the entire screen. Subsequently, the film placement region calculating unit 113 instructs the scan sensor 114 to scan a front surface of the liquid crystal panel 105. Since a film image has been placed on the screen by the time point where the present process is performed, the film placement region calculating unit 113 is to acquire a scanned image representing a state where the film image is placed on the white display patch displayed on the entire screen such as shown in FIG. 7A. Subsequently, the film placement region calculating unit 113 analyzes the acquired scanned image and calculates a region in which the film image is placed on the screen (hereinafter, referred to as a "film placement region").

In this case, a most upper left position in the display region of the screen is set as an origin (0, 0) [pixels], and region information is assumed to be expressed by an X coordinate x [pixels] and a Y coordinate y [pixels] of an upper left corner of the region, a width w [pixels] of the region, and a height h [pixels] of the region. Therefore, the region information of the film placement region is expressed as (xf, yf, wf, hf). In this case, as shown in FIG. 7A, it is assumed that the X coordinate of the upper left corner of the region is xf, the Y coordinate is yf, the width is wf, and the height is hf. Finally, the film placement region calculating unit 113 issues an instruction to the display device GUI generating unit 102 to erase the white display patch and returns the calculated region information (xf, yf, wf, hf) of the film placement region to the display device control unit 110.

In step S704, the display device control unit 110 of the liquid crystal display device 1 issues an instruction to the x-ray film illuminator region determining unit 115 to determine an x-ray film illuminator region in the screen of the liquid crystal display device 1 together with the region information (xf, yf, wf, hf) of the film placement region.

Figure 7B:
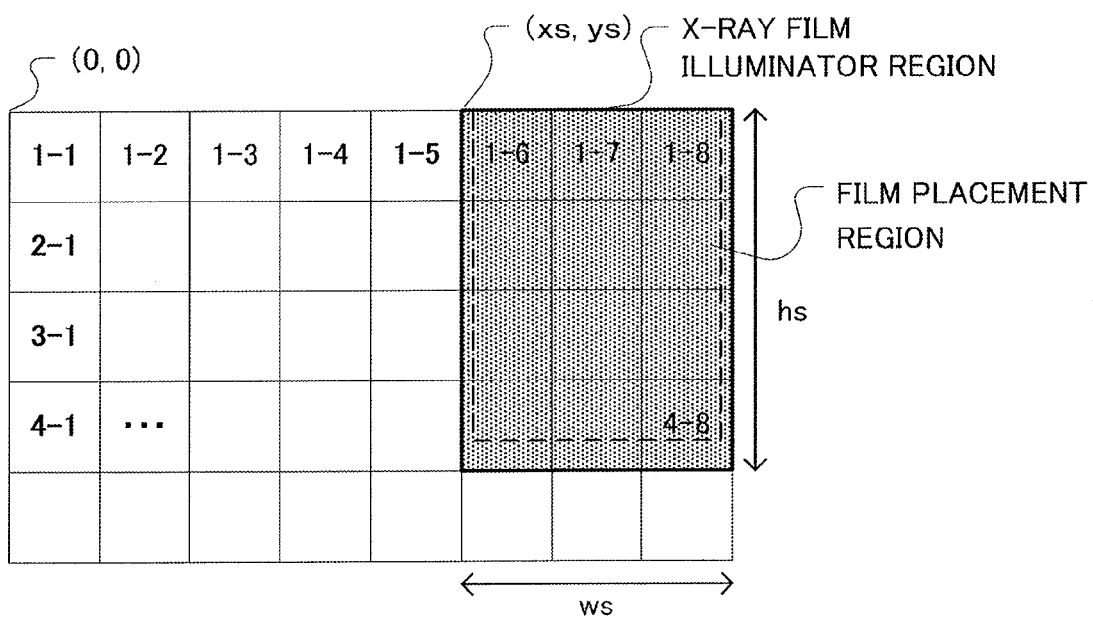

The x-ray film illuminator region determining unit 115 calculates a BL control block to be illuminated as the x-ray film illuminator region based on layout information of BL control blocks of the backlight 111 that is retained in advance and on the region information of the film placement region. The layout information of BL control blocks of the backlight 111 that is retained in advance is the information shown in FIG. 2. The region information of the film placement region is the information expressed as (xf, yf, wf, hf) that is received from the display device control unit 110. The BL control block to be illuminated as the x-ray film illuminator region will be hereinafter referred to as an x-ray film illuminator region BL control block. Since the entire film placement region must be illuminated at high brightness as the x-ray film illuminator region, the BL control blocks in a grayed out portion in FIG. 7B are used as x-ray film illuminator region BL control blocks. More specifically, BL control blocks including the film placement region or, in other words, all BL control blocks having a portion shared with the film placement region are to be used as x-ray film illuminator region BL control blocks. Subsequently, the x-ray film illuminator region determining unit 115 saves information regarding the obtained x-ray film illuminator region BL control blocks.

In step S705, the x-ray film illuminator region determining unit 115 calculates region information of the x-ray film illuminator region in the screen based on layout information of BL control blocks of the backlight 111 that is retained in advance and on the information regarding the x-ray film illuminator region BL control blocks. The information regarding the x-ray film illuminator region BL control blocks is the information acquired in step S704. The x-ray film illuminator region in the screen is the region depicted by the grayed portion in FIG. 7B and region information thereof is expressed by (xs, ys, ws, hs). In this case, as shown in FIG. 7B, it is assumed that the X coordinate of the upper left corner of the x-ray film illuminator region is xf, the Y coordinate is yf, the width is wf, and the height is hf. The x-ray film illuminator region determining unit 115 returns the calculated region information (xs, ys, ws, hs) of the x-ray film illuminator region to the display device control unit 110.

In step S706, the display device control unit 110 of the liquid crystal display device 1 acquires a set brightness of the x-ray film illuminator region and a set brightness of the image display region from the set brightness retaining unit 109.

In step S707, the display device control unit 110 of the liquid crystal display device 1 hands over the region information (xs, ys, ws, hs) of the x-ray film illuminator region acquired in step S705 to the display prohibited region calculating unit 116. In addition, the display device control unit 110 hands over information on the set brightness of the x-ray film illuminator region and the set brightness of the image display region acquired in step S706 to the display prohibited region calculating unit 116. Furthermore, the display device control unit 110 instructs the display prohibited region calculating unit 116 to calculate a display prohibited region.

Upon receiving the instruction from the display device control unit 110, the display prohibited region calculating unit 116 of the liquid crystal display device 1 calculates a distance of influence L [pixels] of light leakage from the x-ray film illuminator region to the image display region. The display prohibited region calculating unit 116 retains a light leakage table shown in FIG. 8. When there is a difference in brightness between adjacent BL control blocks, the light leakage table is information representing a correspondence between the brightness difference and a distance of influence L [pixels] of light leakage to BL control blocks with lower brightness. The light leakage table stores results measured in advance during manufacturing or the like. A distance of influence of light leakage refers to a distance at which a deviation in brightness or chromaticity occurs at a level in excess of a predetermined permissible level in a low brightness side display region among adjacent display regions. A level in excess of a predetermined permissible level is a level where an observer recognizes a deviation in brightness and feels discomfort and is obtained in advance by a measurement experiment or the like. The greater the difference in brightness between the high brightness side and the low brightness side, the greater the influence of light leakage from the high brightness side. For example, if the set brightness acquired in step S706 of the x-ray film illuminator region is 2000 cd/m$^2$ and the set brightness acquired in step S706 of the image display region is 500 cd/m$^2$, then there is a difference in brightness of 1500 cd/m$^2$. In this case, a light leakage influence distance L of 300 pixels is obtained from the light leakage table shown in FIG. 8.

Figure 9A:
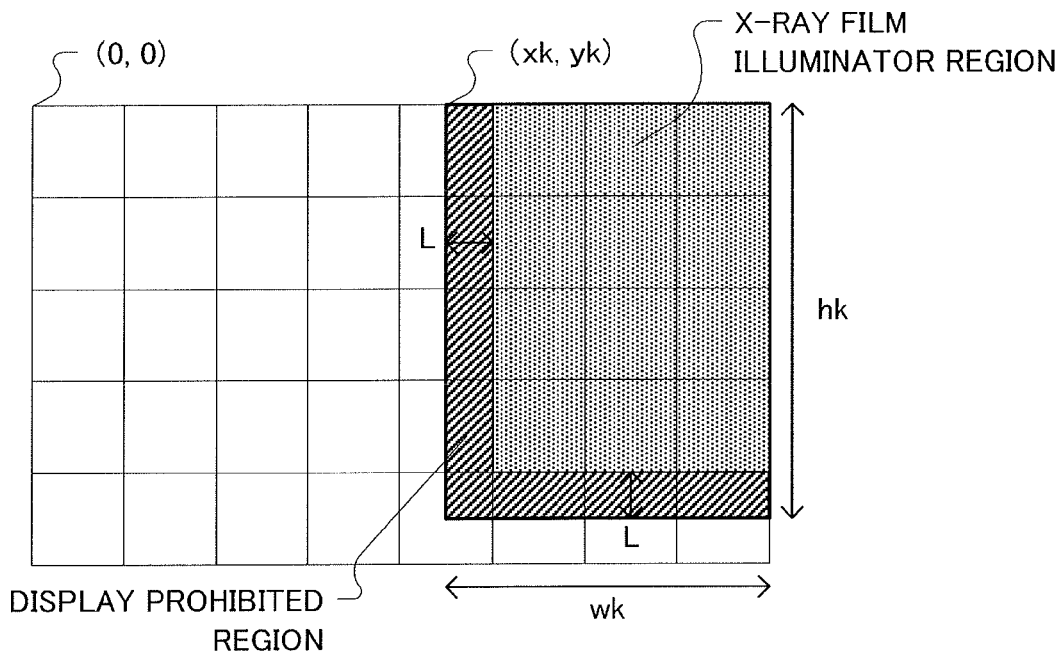
FIGS. 9A and 9B are diagrams showing examples of a digital image display prohibited region and a free region according to the first embodiment.

In step S708, the display prohibited region calculating unit 116 of the liquid crystal display device 1 calculates a display prohibited region from the region information (xs, ys, ws, hs) of the x-ray film illuminator region handed over from the display device control unit 110 and the light leakage influence distance L acquired in step S707. In this case, the display prohibited region is a region that combines the x-ray film illuminator region with a region where color is changed due to the influence of light leakage. In the present embodiment, as shown in FIG. 9A, the display prohibited region is a region (xk, yk, wk, hk) created by adding a range of a predetermined range that is defined by the light leakage influence distance L to the periphery of the x-ray film illuminator region (xs, ys, ws, hs) calculated in step S705. The predetermined range in the periphery of the x-ray film illuminator region is a range in which the influence of like leakage from the x-ray film illuminator region exceeds a predetermined permissible level. In this case, as shown in FIG. 9A, it is assumed that the X coordinate of the upper left corner of the display prohibited region is xk, the Y coordinate is yk, the width is wk, and the height is hk. Finally, the display prohibited region calculating unit 116 returns the region information (xk, yk, wk, hk) of the obtained display prohibited region to the display device control unit 110.

In step S709, the display device control unit 110 of the liquid crystal display device 1 uses the display device communicating unit 106 to transmit the region information (xk, yk, wk, hk) of the display prohibited region obtained in step S708 to the control device 2 as a response to the inquiry instruction with respect to the display prohibited region.

In step S710, the control device communicating unit 207 of the control device 2 receives the region information (xk, yk, wk, hk) of the display prohibited region and notifies the region information (xk, yk, wk, hk) of the display prohibited region to the divided display control unit 211.

Figure 9B:
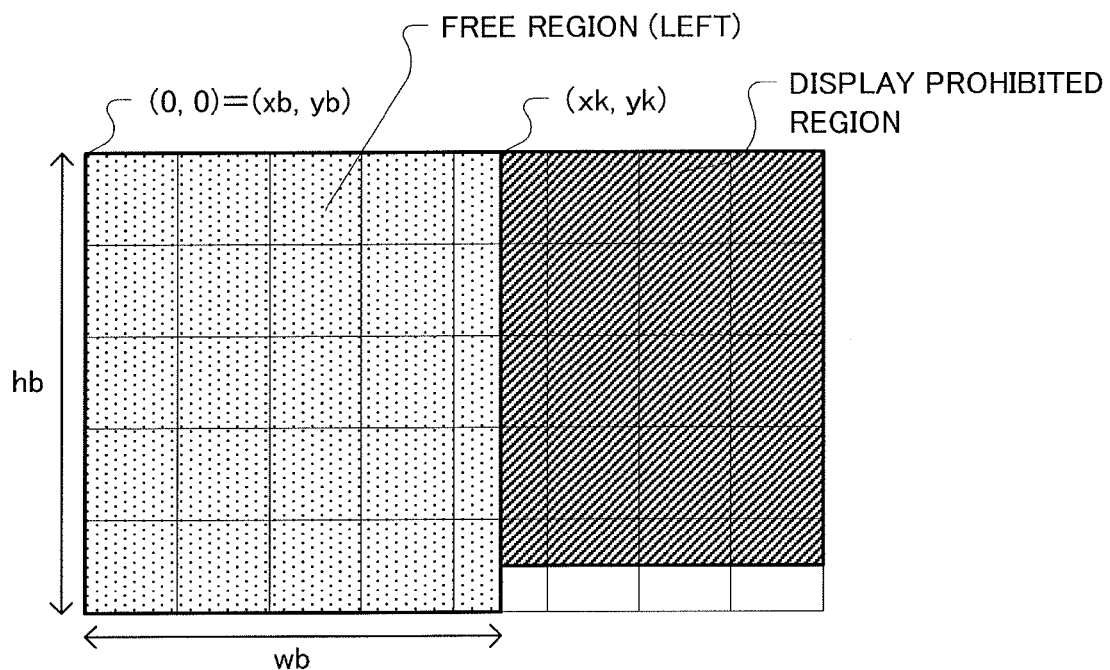

In step S711, the divided display control unit 211 of the control device 2 receives the region information (xk, yk, wk, hk) of the display prohibited region from the control device communicating unit 207 and determines a digital image display region (xb, yb, wb, hb) for displaying a digital image. First, the divided display control unit 211 calculates a free region that is a region created by subtracting the display prohibited region from an entire display region of the screen. In the present embodiment, the free region is a display region adjacent to the left and a display region adjacent to the right of the display prohibited region (xk, yk, wk, hk). When the display prohibited region is as shown in FIG. 9A, since a display region does not exist to the right of the display prohibited region, only the region to the left of the display prohibited region as shown in FIG. 9B constitutes the free region. Next, the divided display control unit 211 determines a region with a greater area between the free region to the right of the display prohibited region and the free region to the left of the display prohibited region as the digital image display region. In the example shown in FIG. 9B, since the only free region is to the left, this free region is determined to be the digital image display region (xb, yb, wb, hb).

In step S712, the divided display control unit 211 of the control device 2 determines a display position of the display image in the digital image display region calculated in step S711. The display position of the digital image is assumed to be a position where comparative diagnosis can be readily performed or, in other words, a position that is as close to the film image as possible. Therefore, when the digital image display region is the right free region, a position that is tangential to an upper left corner of the digital image display region is set as the display position of the display image. In addition, when the digital image display region is the left free region, a position that is tangential to an upper right corner of the digital image display region is set as the display position of the display image. In the example shown in FIG. 9B, since the digital image display region is the left free region, the display position of the display image is a position that is tangential to the upper right corner of the digital image display region.

In step S713, the divided display control unit 211 of the control device 2 hands over the region information (xb, yb, wb, hb) of the digital image display region and information on the display position of the display image obtained in step S712 to the layout unit 203. In the example shown in FIG. 9B, the display position of the display image is a position that is tangential to the upper right corner of the digital image display region. Subsequently, in step S504 of the <Control process of control device control unit 210> shown in FIG. 4A, the divided display control unit 211 issues an instruction to perform layout adjustment on the digital image inputted from the decoding unit 202. The layout unit 203 sends the display image data configured so that a digital image is laid out and displayed in accordance with the instruction to the control device display compositing unit 205. Accordingly, a digital image after a layout process is displayed on the liquid crystal panel 105 of the liquid crystal display device 1.

In step S714, the divided display control unit 211 of the control device 2 uses the control device communicating unit 207 to transmit a control instruction to the liquid crystal display device 1 to operate in a "divided display mode" in which divided display of an x-ray film illuminator region and an image display region is performed.

In step S715, the display device communicating unit 106 of the liquid crystal display device 1 receives the command and notifies the command to the display device control unit 110.

Figure 10A:
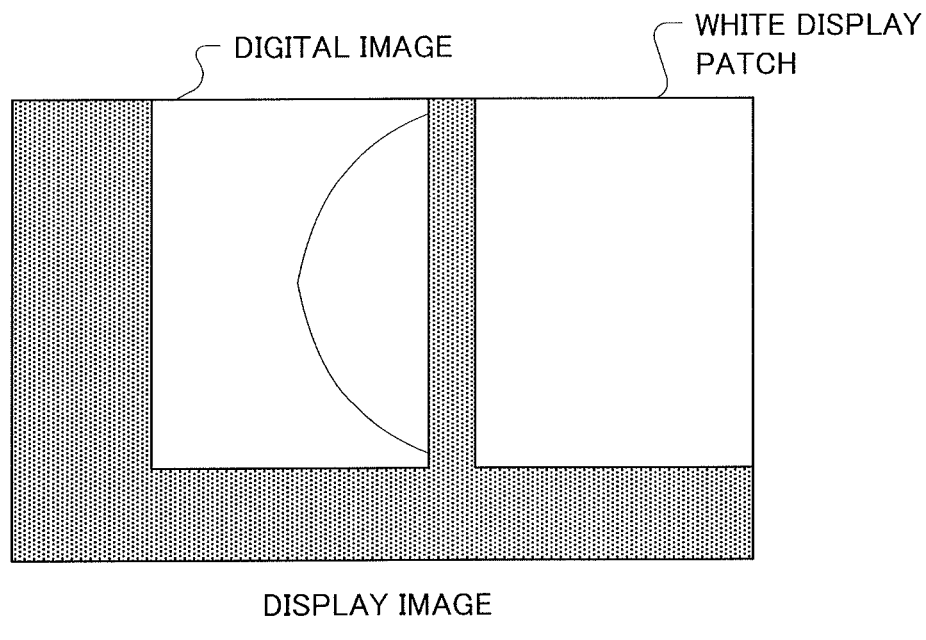
FIGS. 10A and 10B show a display image after a divided display process and a state where a film image is placed according to the first embodiment.
Figure 10B:
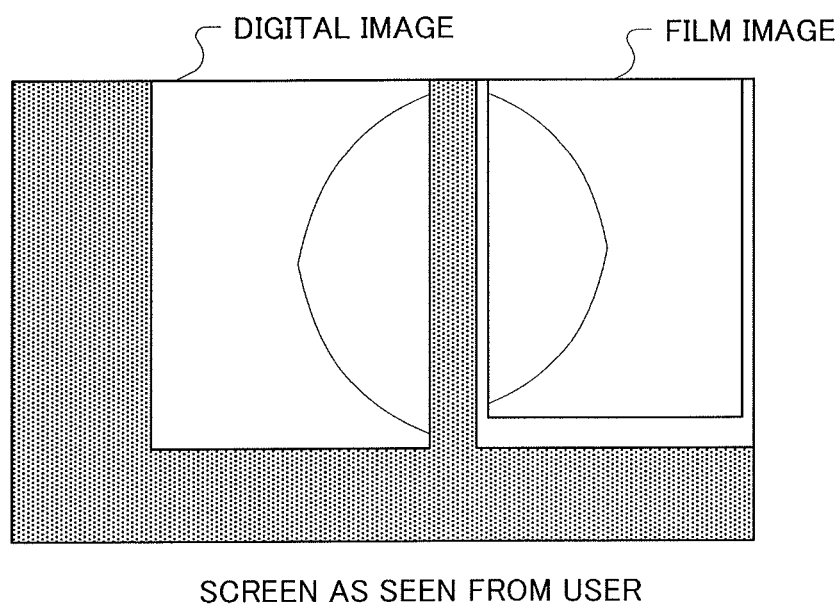

In step S716, upon receiving the instruction to operate in the divided display mode from the display device communicating unit 106, the display device control unit 110 of the liquid crystal display device 1 first hands over region information regarding the x-ray film illuminator region obtained in step S705 to the display device GUI generating unit 102. The region information regarding the x-ray film illuminator region is (xs, ys, ws, hs). In addition, the display device control unit 110 instructs the display device GUI generating unit 102 to display a white display patch for an x-ray film illuminator in the x-ray film illuminator region. The display device GUI generating unit 102 sends the white display patch created in adherence to the instruction to the display device display compositing unit 103 and the white display patch is displayed on the liquid crystal panel 105. The display device display compositing unit 103 composites the digital image after layout created in step S713 and the white display patch created in the present process. As a result, an image in which the digital image and the white display patch are arranged side by side is displayed as shown in FIG. 10A. When the user views the screen of the liquid crystal display device 1, since the film image is placed on the white display patch, the user can view the screen in a state where the digital image and the film image are arranged side by side as shown in FIG. 10B.

In step S717, the display device control unit 110 of the liquid crystal display device 1 hands over the set brightness of the x-ray film illuminator region and the set brightness of the image display region acquired in step S706 to the BL drive control unit 112 and instructs the BL drive control unit 112 to adjust brightness of each BL control block.

Upon receiving the instruction, the BL drive control unit 112 of the liquid crystal display device 1 acquires information on an x-ray film illuminator region BL control block obtained in step S704 from the x-ray film illuminator region determining unit 115. In addition, the BL drive control unit 112 causes the x-ray film illuminator region BL control blocks to emit light at the set brightness of the x-ray film illuminator region and the BL control blocks belonging to regions other than the x-ray film illuminator to emit light at the set brightness of the image display region. According to the process described above, the liquid crystal display device 1 starts operating in the divided display mode and divided display of the x-ray film illuminator region and the image display region is realized.

In step S718, the display device control unit 110 of the liquid crystal display device 1 uses the display device communicating unit 106 to transmit a message informing that an operation start process in the divided display mode has finished to the control device 2.

In step S719, the control device communicating unit 207 of the control device 2 receives the message informing that the operation start process in the divided display mode has finished and notifies the message to the divided display control unit 211.

The divided display control unit 211 of the control device 2 receives the message informing finish of operation of the liquid crystal display device 1 in the divided display mode from the control device communicating unit 207 and concludes the present process.

As described above, with the comparative diagnosis system according to the present embodiment, when performing comparative diagnosis by arranging and displaying a digital image and a film image in a single screen, the digital image is automatically laid out and displayed at a position as close to an x-ray film illuminator region as possible in accordance with a placement position of the film image. Therefore, since a user operation for manually moving a display position of the digital image to a position adjacent to the placement position of the film image is no longer required, the digital image and the film image can be arranged side by side for observation in an efficient manner. As a result, convenience is improved.

In addition, since the comparative diagnosis device according to the present embodiment displays a digital image in a region that is not influenced by light leakage from the x-ray film illuminator region, the digital image can be accurately displayed.

Moreover, in the first embodiment described above, a digital image displayed in advance in the screen is used as the digital image displayed during divided display as described with reference to the process flow titled <Determination process of display digital image> (FIG. 4B) that is performed by the display image determining unit 208 of the control device 2. Alternatively, a GUI (not shown) that enables the user to select a digital image to be displayed may be displayed and a digital image selected by the user may be display.

While an example in which the scan sensor 114 of the liquid crystal display device 1 is used to detect a film placement region has been described in the first embodiment, a method of detecting a film placement region is not limited thereto. For example, a configuration may be adopted in which a touch panel is installed on a front surface of the liquid crystal panel 105 of the liquid crystal display device 1 and the user is capable of inputting information regarding a film placement region by a touch operation. In this case, for example, information regarding a film placement region can be inputted by touching positions of the four apexes of a film.

In addition, an example in which a light leakage table such as that shown in FIG. 8 is referenced when calculating a light leakage influence distance in step S707 of the flow titled <Divided display process> has been described in the first embodiment. Alternatively, a light leakage influence distance may be calculated according to a process of outputting light leakage influence distance in response to an input of a difference in set brightness between the x-ray film illuminator region and the image display region using an approximation expression representing a relationship between a difference in brightness and a light leakage influence distance.

Second Embodiment

For the present embodiment, an example will be described in which a single comparative diagnosis device constitutes the comparative diagnosis system according to the first embodiment which is constituted by the liquid crystal display device 1 and the control device 2.

The present embodiment will be described with a focus on a difference from the first embodiment. The same reference numerals as the first embodiment will be used for portions with the same contents as the first embodiment.

Figure 11:
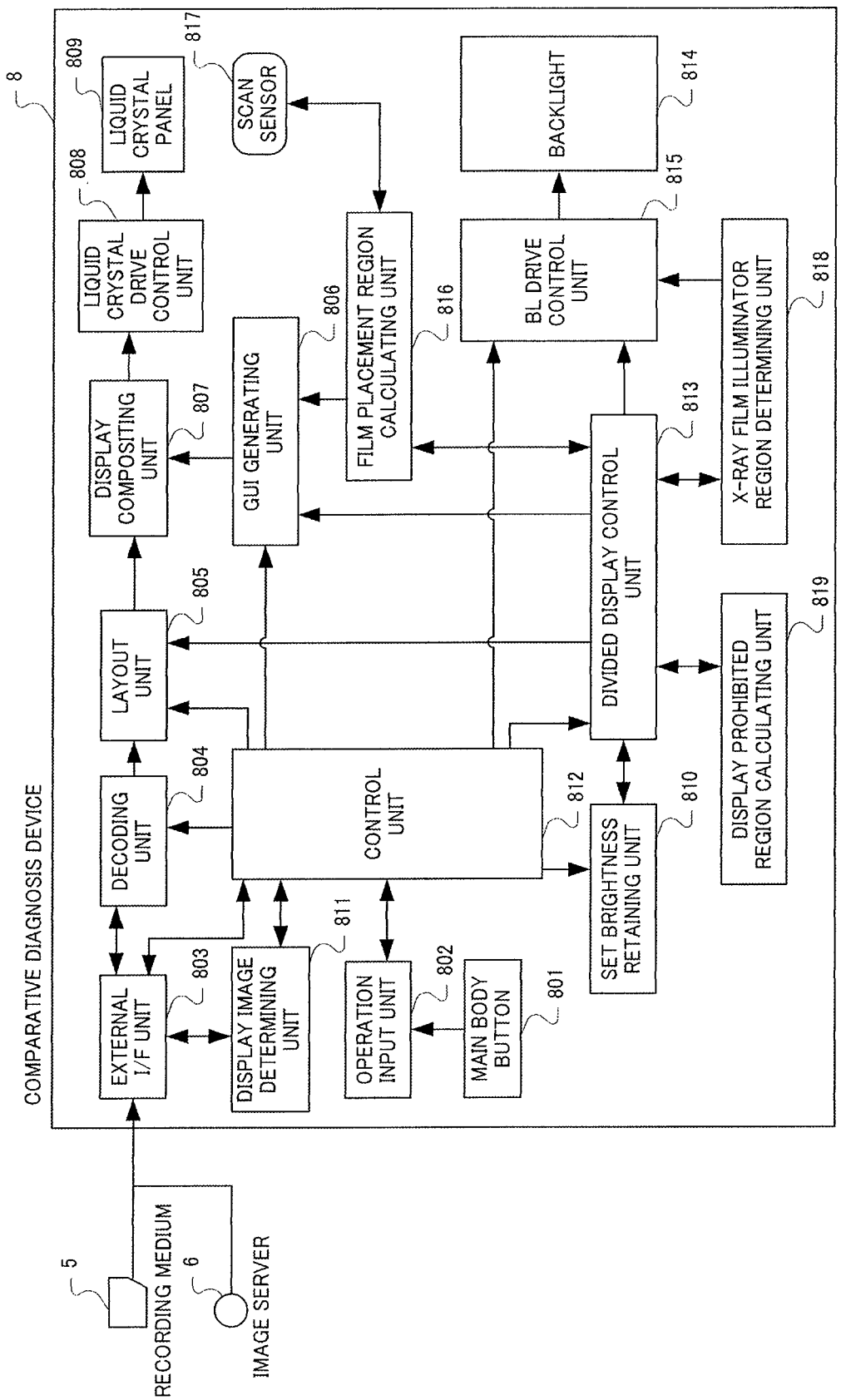
FIG. 11 is a block diagram showing a configuration of a comparative diagnosis device according to a second embodiment.

Hereinafter, the present embodiment will be described with reference to the drawings. FIG. 11 shows an example of a configuration of a comparative diagnosis system to which the present invention is applied. The comparative diagnosis system is constituted by a comparative diagnosis device 8, the recording medium 5, and the image server 6.

A medical monitor (an image display device) used for diagnosis is assumed as the comparative diagnosis device 8. The comparative diagnosis device 8 reads medical digital image data from the recording medium 5 or the image server 6 and displays the medical digital image data in a screen. The comparative diagnosis device 8 is a liquid crystal display device equipped with a local dimming function and is capable of individually adjusting backlight brightness for each region during divided display of an x-ray film illuminator region and an image display region using the local dimming function.

Next, respective functional blocks of the comparative diagnosis device 8 will be described.

A main body button 801 is an operation button for performing an operation to input an instruction to the comparative diagnosis device 8.

An operation input unit 802 recognizes a user operation performed using the main body button 801 and transmits operation contents to the control unit 812 (to be described later).

An external I/F unit 803 is an interface with the recording medium 5 and the image server 6 and reads digital image data in the recording medium 5 or the image server 6 in response to an instruction from the decoding unit 804 (to be described later).

The decoding unit 804 performs a decoding process on digital image data acquired via the external I/F unit 803 and transmits decoded image data to a layout unit 805 (to be described later).

The layout unit 805 receives a layout instruction from a control unit 812 or a divided display control unit 813 (to be described later) and performs a layout process on image data received from the decoding unit 804. In this case, for example, contents of a layout instruction include designation of a position such as "center of screen" and designation of a display region (a horizontal coordinate x and a vertical coordinate y of an origin, a width w, and a height h) of image data in the screen. A layout process is a process of performing scaling and arrangement in order to display an image based on image data at a position or in a display region designated by a layout instruction.

A GUI generating unit 806 generates image data for displaying a GUI such as a warning and a message in response to an instruction from the control unit 812 and transmits the image data to a display compositing unit 807 (to be described later). In addition, the GUI generating unit 806 also receives an instruction to generate a white display patch for an x-ray film illuminator region from the divided display control unit 813, creates a white display patch in an instructed size, and transmits the white display patch to the display compositing unit 807.

The display compositing unit 807 composites image data inputted from the layout unit 805 and image data for GUI display inputted from the GUI generating unit 806 and transmits the obtained image data to a liquid crystal drive control unit 808.

The liquid crystal drive control unit 808 converts the image data inputted from the display compositing unit 807 into a control signal for a liquid crystal panel 809 (to be described later) and transmits the image data to the liquid crystal panel 809 to perform display control of the liquid crystal panel 809.

The liquid crystal panel 809 receives the control signal from the liquid crystal drive control unit 808, and by driving liquid crystals according to the control signal, displays an image on the panel.

A set brightness retaining unit 810 is a memory that retains (stores) a set brightness of an x-ray film illuminator region and a set brightness of an image display device. The set brightness of both regions can be changed at will by the user by operating the main body button 801. Alternatively, a GUI (not shown) for changing set brightness may be displayed during an operation of the main body button 801. The control unit 812 interprets contents of a user operation and saves a changed set brightness by writing information on the inputted set brightness into the set brightness retaining unit 810.

A display image determining unit 811 receives an instruction from the control unit 812 (to be described later) and determines a digital image that is automatically displayed during divided display. A detail process will be described in <Display digital image determination process> to be presented below.

By causing the decoding unit 804 to read and perform a decoding process on appropriate digital image data in accordance with a user operation, the control unit 812 causes a digital image designated by the user in the screen and performs management of the digital image that is being displayed. In addition, the control unit 812 also performs control of the comparative diagnosis device 8 in general such as a process for writing a set brightness changed by a user operation into the set brightness retaining unit 810 and a process for causing the GUI generating unit 806 to output image data for GUI display. Furthermore, when an instruction to perform divided display of an x-ray film illuminator region and an image display device is inputted by a user operation using the main body button 801, the control unit 812 realizes divided display using the divided display control unit 813 (to be described later). A detailed process of divided display will be described in a flow titled <Control process of control unit 812> to be presented later.

The divided display control unit 813 receives a divided display instruction from the control unit 812 and performs a process for realizing divided display of an x-ray film illuminator region and an image display region using a film placement region calculating unit 816, an x-ray film illuminator region determining unit 818, and a display prohibited region calculating unit 819 (to be described later). At this point, the divided display control unit 813 performs control so as to lay out and display a digital image at a position which is not influenced by light leakage from an x-ray film illuminator region and which is as close to the x-ray film illuminator region as possible. A detailed process will be described in the flow titled <Divided display process> to be presented below.

The backlight 814 includes a plurality of LEDs as light sources in a matrix pattern and is installed in a rear part of the liquid crystal panel 809. As shown in FIG. 2, the backlight 814 is constituted by a plurality of BL control blocks which are respectively assigned a BL control block number.

The BL drive control unit 815 performs a process for controlling emission brightness of each BL control block of the backlight 814 in accordance with an instruction from the divided display control unit 813.

In accordance with an instruction from the divided display control unit 813, the film placement region calculating unit 816 calculates a film placement region of the screen of the comparative diagnosis device 8 using a scan sensor 817 (to be described later).

The scan sensor 817 is a driven two-dimensional image sensor installed on a front surface of the liquid crystal panel 809. Under control by the film placement region calculating unit 816, the scan sensor 817 scans the front surface of the liquid crystal panel 809 and creates a scanned image. When a film image is placed on the front surface of the liquid crystal panel 809 during execution of scanning by the scan sensor 817, a scanned image including the film image is created. By analyzing the scanned image including the film image, the film placement region calculating unit 816 is capable of detecting a placement position of the film image.

In accordance with an instruction from the divided display control unit 813, the x-ray film illuminator region determining unit 818 determines a BL control block to be used as an x-ray film illuminator region and a region in the screen to be used as an x-ray film illuminator region.

In accordance with an instruction from the divided display control unit 813, the display prohibited region calculating unit 819 calculates a display prohibited region with respect to a digital image in the screen of the comparative diagnosis device 8 during divided display. A display prohibited region is a region that combines an x-ray film illuminator region with a region in which a digital image cannot be accurately displayed due to light leakage from the x-ray film illuminator region. A detailed process will be described in the flow titled <Divided display process> to be presented below.

While there are blocks other than those described above for executing basic functions as a comparative diagnosis device, description of such blocks will be omitted herein.

Next, a divided display process of the comparative diagnosis device 8 according to the present embodiment will be described with reference to the flow charts shown in FIGS. 4A, 4B, and 12.

As shown in FIG. 6A, let us assume that a medical digital image read from the recording medium 5 or the image server 6 is displayed in the screen of the comparative diagnosis device 8 and is used for diagnosis prior to performing divided display. In the comparative diagnosis device 8, the control unit 812 uses the decoding unit 804 to decode the digital image data acquired from the recording medium 5 or the image server 6 and issues a layout instruction to the layout unit 805 so that the digital image is to be displayed in an arbitrary size at "center of screen". The comparative diagnosis device 8 creates image data for performing display such as shown in FIG. 6A. In addition, the comparative diagnosis device 8 further instructs the BL drive control unit 815 to cause all BL control blocks to emit light at the set brightness of the image display device read from the set brightness retaining unit 810. Accordingly, a digital image display state shown in FIG. 6A is realized.

A film clip for holding and fixing a film image such as that shown in FIG. 6A is provided in an upper part of the liquid crystal panel 809 of the comparative diagnosis device 8 and is used when the user places the film image.

It is assumed that a timing at which the comparative diagnosis device 8 starts divided display is a timing at which a GUI (not shown) for setting ON/OFF of divided display is displayed and the user performs an operation to set divided display=ON on the GUI using the main body button 801.

<Control Process of Control Unit 812>

First, a process of the control unit 812 will be described using the flow chart shown in FIG. 4A.

It is assumed that the flow chart shown in FIG. 4A starts at a time point where, in a state in which only a digital image is displayed in the screen such as shown in FIG. 6A, the control unit 812 detects that divided display=ON has been set.

In step S501, the control unit 812 issues an instruction to the GUI generating unit 806 to generate a GUI for prompting placement of a film image. As a result of this process, a GUI such as that shown in FIG. 6B is displayed on the screen (the liquid crystal panel 809) of the comparative diagnosis device 8.

In step S502, the control unit 812 determines whether or not the film image has been placed on the screen. In the present embodiment, this determination is made based on whether or not an operation (for example, pressing of an <Enter> button (not shown)) has been performed by the user using the main body button 801 to input completion of film placement to the comparative diagnosis device 8 during display of the GUI shown in FIG. 6B. When the operation has been performed, the control unit 812 determines that the film image has been placed and advances the process to step S503 after erasing the GUI. When the operation has not been performed, the control unit 812 determines that the film image has not been placed and returns the process to step S501.

In step S503, the control unit 812 issues an instruction to the display image determining unit 811 to determine a digital image to be displayed when performing divided display (hereinafter, referred to as a display digital image) and acquires a file path to the display digital image.

In step S504, the control unit 812 instructs the decoding unit 804 to read and decode image data at the file path of the display digital image acquired in step S503. Upon receiving the instruction, the decoding unit 804 reads and decodes the image data at the file path of the display digital image and transmits the decoded image data to the layout unit 805.

In step S505, the control unit 812 issues an instruction to the divided display control unit 813 to perform divided display and ends the process.

<Determination Process of Display Digital Image>

Next, a determination process performed by the display image determining unit 811 of a digital image (display digital image) to be automatically displayed during divided display will be described with reference to the flow chart shown in FIG. 4B. In the present embodiment, a digital image that is displayed when divided display=0 is set is determined as a display digital image.

The flow chart shown in FIG. 4B represents details of the process performed in step S503 in the flow chart shown in FIG. 4A. It is assumed that the flow chart shown in FIG. 4B is executed at a time point where the display image determining unit 811 receives a determination instruction of a display digital image from the control unit 812.

In step S601, the display image determining unit 811 acquires a file path of a digital image currently being displayed from the control unit 812.

In step S602, the display image determining unit 811 returns the file path acquired in step S601 to the control unit 812 and ends the process.

According to the process described above, a digital image that is being displayed at the moment where divided display=ON is set can be determined as a display digital image and a file path of the display digital image can be returned to the control unit 812.

<Divided Display Process>

Next, a divided display process performed by the divided display control unit 813, the x-ray film illuminator region determining unit 818, and the display prohibited region calculating unit 819 will be described with reference to the flow chart shown in FIG. 12.

Figure 12:
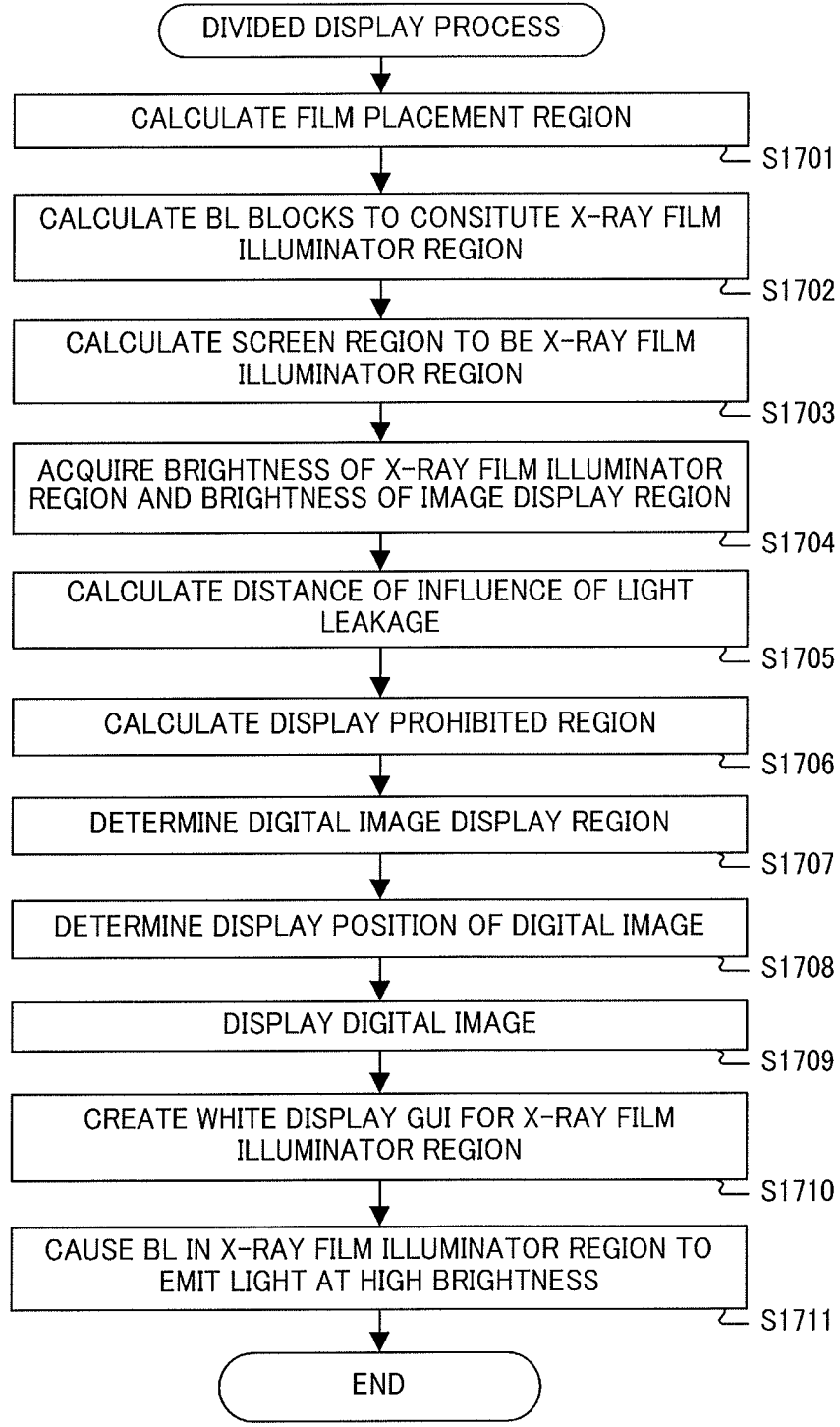
FIG. 12 is a flow chart showing a processing procedure of divided display according to the second embodiment.

The flow chart shown in FIG. 12 represents details of the process performed in step S505 in the flow chart shown in FIG. 4A. It is assumed that the flow chart shown in FIG. 12 is executed at a time point where the divided display control unit 813 receives a divided display instruction from the control unit 812.

In step S1701, the divided display control unit 813 issues an instruction to calculate a film placement region to the film placement region calculating unit 816.

Upon receiving the instruction from the divided display control unit 813, the film placement region calculating unit 816 instructs the GUI generating unit 806 to create a white display patch to be displayed on the entire screen and instructs the scan sensor 817 to scan the front surface of the liquid crystal panel 809. Since a film image has been placed on the screen by the time point where the present process is performed, the film placement region calculating unit 816 is to acquire a scanned image representing a state where the film image is placed on the white display patch displayed on the entire screen such as shown in FIG. 7A. Subsequently, the film placement region calculating unit 816 analyzes the acquired scanned image and calculates region information (xf, yf, wf, hf) of the film placement region in the screen. Finally, the film placement region calculating unit 816 issues an instruction to the GUI generating unit 806 to erase the white display patch and returns the calculated region information (xf, yf, wf, hf) of the film placement region to the divided display control unit 813.

In step S1702, the divided display control unit 813 issues an instruction to the x-ray film illuminator region determining unit 818 to determine an x-ray film illuminator region together with the region information (xf, yf, wf, hf) of the film placement region calculated in S1701.

The x-ray film illuminator region determining unit 818 calculates an x-ray film illuminator region BL control block based on layout information of BL control blocks of the backlight 814 that is retained in advance and on the region information of the film placement region acquired in step S1701. The layout information of the BL control blocks of the backlight 814 is as shown in FIG. 2. The region information of the film placement region is (xf, yf, wf, hf). Since the entire film placement region must be illuminated at high brightness as the x-ray film illuminator region, the BL control blocks in a gray portion in FIG. 7B are used as x-ray film illuminator region BL control blocks.

In step S1703, the x-ray film illuminator region determining unit 818 calculates region information of the x-ray film illuminator region in the screen based on layout information of BL control blocks of the backlight 814 that is retained in advance and on the information regarding the x-ray film illuminator region BL control blocks. The information regarding the x-ray film illuminator region BL control blocks is the information acquired in step S1702. The region information regarding the x-ray film illuminator region in the screen is (xs, ys, ws, hs). The x-ray film illuminator region determining unit 818 returns the calculated region information (xs, ys, ws, hs) to the divided display control unit 813.

In step S1704, the divided display control unit 813 acquires a set brightness of the x-ray film illuminator region and a set brightness of the image display region from the set brightness retaining unit 810.

In step S1705, the divided display control unit 813 hands over the region information (xs, ys, ws, hs) of the x-ray film illuminator region and information on the set brightness of the x-ray film illuminator region and the set brightness of the image display region to the display prohibited region calculating unit 819. Furthermore, the divided display control unit 813 instructs the display prohibited region calculating unit 819 to calculate a display prohibited region. The region information (xs, ys, ws, hs) regarding the x-ray film illuminator region is the region information acquired in step S1703. Information on the set brightness of the x-ray film illuminator region and the set brightness of the image display region is information acquired in step S1705.

Upon receiving the instruction from the divided display control unit 813, the display prohibited region calculating unit 819 calculates a distance of influence L [pixels] of light leakage from the x-ray film illuminator region to the image display region. The display prohibited region calculating unit 819 retains a light leakage table such as that shown in FIG. 8. For example, if the set brightness acquired in step S1704 of the x-ray film illuminator region is 2000 $cd/m^2$ and the set brightness acquired in step S1704 of the image display region is 500 $cd/m^2$, then there is a difference in brightness of 1500 $cd/m^2$. In this case, a light leakage influence distance L of 300 pixels is obtained from the light leakage table shown in FIG. 8.

In step S1706, the display prohibited region calculating unit 819 calculates a display prohibited region from the region information (xs, ys, ws, hs) of the x-ray film illuminator region handed over from the divided display control unit 813 and information on the light leakage influence distance L acquired in step S1705. In the present embodiment, as shown in FIG. 9A, the display prohibited region is a region (xk, yk, wk, hk) created by adding a range of a predetermined range that is defined by the light leakage influence distance L to the periphery of the x-ray film illuminator region (xs, ys, ws, hs) calculated in step S1703. Finally, the display prohibited region calculating unit 819 returns the region information (xk, yk, wk, hk) of the obtained display prohibited region to the divided display control unit 813.

In step S1707, the divided display control unit 813 determines a digital image display region (xb, yb, wb, hb) for displaying a digital image using the region information (xk, yk, wk, hk) of the display prohibited region obtained in step S1706. First, the divided display control unit 813 calculates a free region that is a region created by subtracting the display prohibited region from an entire display region of the screen. In the present embodiment, the free region is a display region adjacent to the left and a display region adjacent to the right of the display prohibited region (xk, yk, wk, hk). When the display prohibited region is as shown in FIG. 9A, since a display region does not exist to the right of the display prohibited region, only the region to the left of the display prohibited region as shown in FIG. 9B constitutes the free region. Next, the divided display control unit 813 determines a region with a greater area between the free region to the right of the display prohibited region and the free region to the left of the display prohibited region as the digital image display region. In the example shown in FIG. 9B, since the only free region is to the left, this free region is determined to be the digital image display region (xb, yb, wb, hb).

In step S1708, the divided display control unit 813 determines a display position of the display image in the digital image display region calculated in step S1707. The display position of the digital image is assumed to be a position where comparative diagnosis can be readily performed or, in other words, a position that is as close to the film image as possible. Therefore, when the digital image display region is the right free region, a position that is tangential to an upper left corner of the digital image display region is set as the display position of the display image. In addition, when the digital image display region is the left free region, a position that is tangential to an upper right corner of the digital image display region is set as the display position of the display image. In the example shown in FIG. 9B, since the digital image display region is the left free region, the display position of the display image is a position that is tangential to the upper right corner of the digital image display region.

In step S1709, the divided display control unit 813 hands over the region information (xb, yb, wb, hb) of the digital image display region and information on the display position of the display image obtained in step S1708 to the layout unit 805. In the example shown in FIG. 9B, the display position of the display image is a position that is tangential to the upper right corner of the digital image display region. Subsequently, in step S504 of the <Control process of control unit 812>, the divided display control unit 813 issues an instruction to perform layout adjustment on the digital image inputted from the decoding unit 804. The layout unit 805 sends the display image data configured so that a digital image is laid out and displayed in accordance with the instruction to the display compositing unit 807. Accordingly, a digital image after a layout process is displayed on the liquid crystal panel 809.

In step S1710, the divided display control unit 813 hands over the region information (xs, ys, ws, hs) on the x-ray film illuminator region to the GUI generating unit 806 and instructs the GUI generating unit 806 to display a white display patch for an x-ray film illuminator in the x-ray film illuminator region. The GUI generating unit 806 sends the white display patch created in adherence to the instruction to the display compositing unit 807 and the white display patch is displayed on the liquid crystal panel. The display compositing unit 807 composites the image created in step S1709 and the white display patch created in the present process. As a result, as shown in FIG. 10A, an image in which the digital image and the white display patch are arranged side by side is displayed. When the user views the screen of the comparative diagnosis device 8, since the film image is placed on the white display patch, the user can view the screen in a state where the digital image and the film image are arranged side by side as shown in FIG. 10B.

In step S1711, the divided display control unit 813 hands over information on the x-ray film illuminator region BL control blocks obtained in step S1702 and information on the set brightness of the x-ray film illuminator region and the set brightness of the image display region acquired in step S1704 to the BL drive control unit 815. In addition, the divided display control unit 813 instructs the BL drive control unit 815 to adjust brightness of each BL control block. The BL drive control unit 815 causes the x-ray film illuminator region BL control blocks to emit light at the set brightness of the x-ray film illuminator region and the BL control blocks belonging to regions other than the x-ray film illuminator to emit light at the set brightness of the image display region.

As described above, with the comparative diagnosis device according to the present embodiment, when performing comparative diagnosis by arranging and displaying a digital image and a film image in a single screen, the digital image is automatically laid out and displayed at a position as close to an x-ray film illuminator region as possible in accordance with a placement position of the film image. Therefore, since a user operation for manually moving a display position of the digital image to a position adjacent to the placement position of the film image is no longer required, the digital image and the film image can be arranged side by side for observation in an efficient manner. As a result, convenience is improved.

In addition, since the comparative diagnosis device according to the present embodiment displays a digital image in a region that is not influenced by light leakage from the x-ray film illuminator region, the digital image can be accurately displayed.

Moreover, in the second embodiment described above, a digital image displayed in advance in the screen is used as the digital image displayed during divided display as described with reference to the <Determination process of display digital image> that is performed by the display image determining unit 811. Alternatively, a GUI (not shown) that enables the user to select a digital image to be displayed may be displayed and a digital image selected by the user may be display.

While an example in which the scan sensor 817 is used to detect a film placement region has been described in the second embodiment, a method of detecting a film placement region is not limited thereto. For example, a configuration may be adopted in which a touch panel is installed on a front surface of the liquid crystal panel 809 and the user is capable of inputting information regarding a film placement region by a touch operation.

Third Embodiment

Next, a third embodiment to which the present invention is applied will be described. In the present embodiment, various methods of selecting a display digital image and methods of realizing such selection in the comparative diagnosis system according to the first embodiment will be illustratively described. In the first embodiment, an example has been described in which, when switching from an image display mode that uses an entire display region as an image display region to a divided display mode that displays an image display region and an x-ray film illuminator region next to one another, one digital image displayed in the image display mode is adopted as a display digital image. In the present embodiment, three methods of determining a display digital image when a plurality of digital images are being displayed at the start of the divided display mode including determination methods 1 to 3 will be illustratively described.

The present embodiment will be described with a focus on a difference from the first embodiment. The same reference numerals as the first embodiment will be used for portions with the same contents as the first embodiment.

Hereinafter, the present embodiment will be described with reference to the drawings.

In a similar manner to the first embodiment, the comparative diagnosis system according to the present embodiment is constituted by the liquid crystal display device 1, the control device 2, the image signal line 3, and the communication signal line 4 (FIG. 2).

Figure 13:
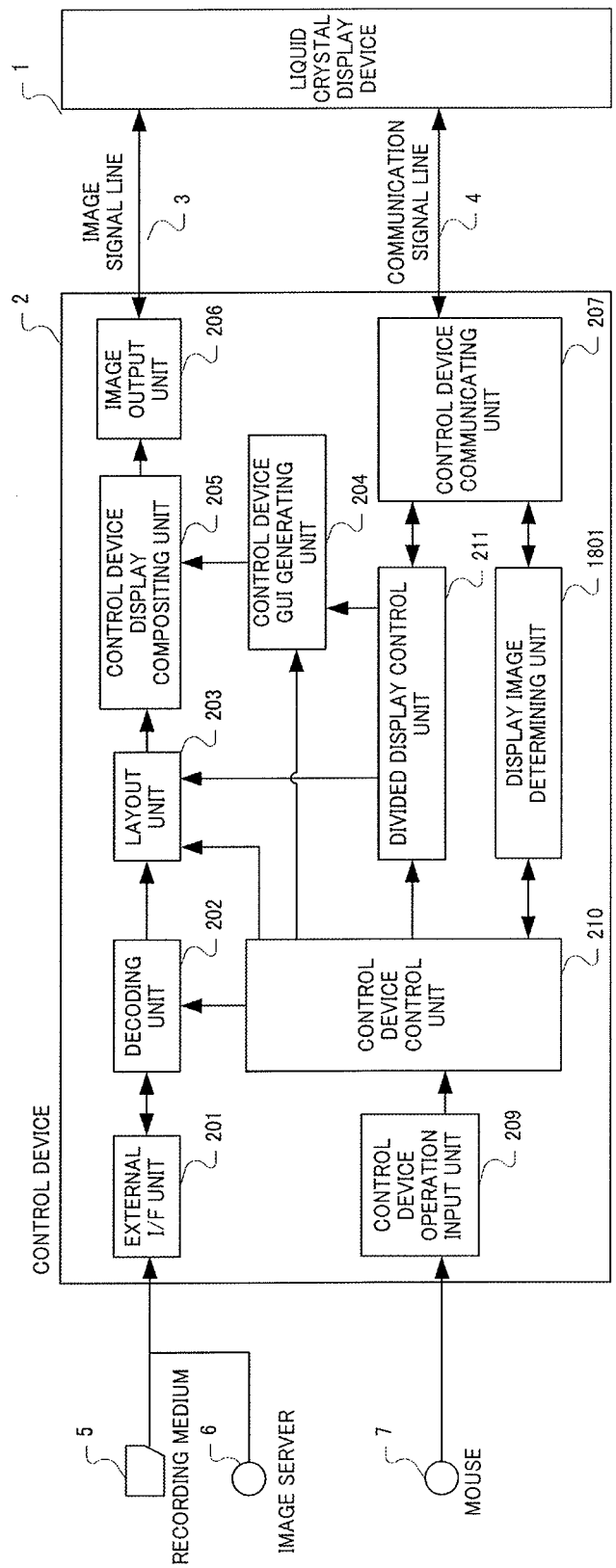
FIG. 13 is a block diagram showing a configuration of a control device according to a third embodiment.

Next, functional blocks of the control device 2 according to the present embodiment will be described with reference to FIG. 13 with a focus on a difference from the first embodiment.

A display image determining unit 1801 receives an instruction from the control device control unit 210 and determines a digital image that is automatically displayed during divided display in a similar manner to the display image determining unit 208 according to the first embodiment. Furthermore, upon determining a display digital image, the display image determining unit 1801 also acquires necessary information from the liquid crystal display device 1 via the control device communicating unit 207. A detailed process of the display image determining unit 1801 will be described in flows presented below.

Next, three types of processes for determining a display digital image from determination method 1 to determination method 3 will be described with reference to the flow charts shown in FIGS. 14 to 16. The flow charts shown in FIGS. 14 to 16 respectively represent details of the process performed in step S503 in the flow chart shown in FIG. 4A. It is assumed that this process is executed from a time point where the display image determining unit 1801 receives an instruction to determine a display digital image from the control device control unit 210. Since processes for realizing divided display other than the process of determining a display digital image (the <control process of control device control unit 210> and the <divided display process>) are similar to those of the first embodiment, a description thereof will be omitted.

Figure 17A:
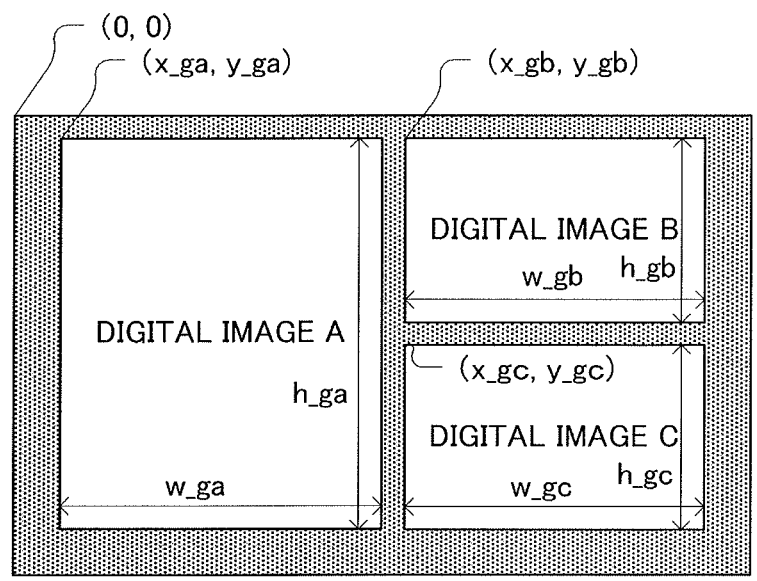
FIGS. 17A and 17B are diagrams showing an example of a screen and a placement position of a film image prior to divided display according to the third embodiment.

As shown in FIG. 17A, let us assume a state exists where multiple medical digital images read from the recording medium 5 or the image server 6 are displayed in the screen of the liquid crystal display device 1 and is used for diagnosis prior to performing divided display. Such a display state is realized by processes described below. Specifically, the control device control unit 210 of the control device 2 uses the decoding unit 202 to decode digital images A, B, and C read from the recording medium 5 or the image server 6. Furthermore, the control device control unit 210 instructs the layout unit 203 to lay out the image A in region (x_ga, y_ga, w_ga, h_ga). In addition, the control device control unit 210 instructs the layout unit 203 to lay out the image B in region (x_gb, y_gb, w_gb, h_gb). Furthermore, the control device control unit 210 instructs the layout unit 203 to lay out the image C in region (x_gc, y_gc, w_gc, h_gc).

<Determination Process of Display Digital Image (Determination Method 1)>

First, a first determination method (hereinafter, referred to as determination method 1) of a display digital image when a plurality of digital images are being displayed at the start of the divided display mode will be described.

The determination method 1 is a method in which an image displayed over a largest area among the plurality of digital images displayed in the screen at a time point of start of divided display of an x-ray film illuminator region and an image display region is adopted as a display digital image. This is based on an assumption that the image displayed over a largest area among the plurality of displayed digital images is most likely to be mainly used for diagnosis and is most likely to be used for a comparative diagnosis with a film image.

A process performed by the display image determining unit 1801 according to the determination method 1 will be described with reference to the flow chart shown in FIG. 14.

In step S1901, the display image determining unit 1801 of the control device 2 inquires about file paths of all digital images that are currently being displayed to the control device control unit 210. In the example shown in FIG. 17A, the display image determining unit 1801 acquires file paths for the digital images A, B, and C from the control device control unit 210.

In step S1902, the display image determining unit 1801 of the control device 2 hands over the file paths for the digital images A, B, and C that are currently being displayed to the control device control unit 210 and acquires region information on respective display regions of the digital images A, B, and C. In the example shown in FIG. 17A, the display image determining unit 1801 acquires the display region (x_ga, y_ga, w_ga, h_ga) of the image A. The display image determining unit 1801 also acquires the display region (x_gb, y_gb, w_gb, h_gb) of the image B. The display image determining unit 1801 also acquires the display region (x_gc, y_gc, w_gc, h_gc) of the image C.

In step S1903, the display image determining unit 1801 of the control device 2 calculates a display area of each image from the region information on the display regions of the digital images A, B, and C acquired in step S1902.

In step S1904, the display image determining unit 1801 of the control device 2 compares the display areas of the digital images A, B, and C acquired in step S1903 and determines the image with the largest display area (in the example shown in FIG. 17A, the digital image A) to be the display digital image. Subsequently, the display image determining unit 1801 hands over the file path of the determined display digital image (in the present embodiment, the digital image A) to the control device control unit 210 and finishes the process.

As a result, an image displayed over a largest area (in the present embodiment, the digital image A) among the plurality of digital images displayed in the screen at the start of the divided display mode can be determined to be a display digital image.

<Determination Process of Display Digital Image (Determination Method 2)>

Next, a second determination method (hereinafter, referred to as determination method 2) of a display digital image when a plurality of digital images are being displayed at the start of the divided display mode will be described.

The determination method 2 is a method in which an image displayed over a largest area in a region excluding a film placement region among the plurality of digital images displayed in the screen at a time point of start of divided display of an x-ray film illuminator region and an image display region is adopted as a display digital image. This is because it is highly likely that a portion overlapping with and hidden by a film image placed by the user among the plurality of displayed images is not used for a comparative diagnosis with the film image. Therefore, it is assumed that the image displayed over a largest area in a region that is not hidden is most likely to be used for comparative diagnosis.

A process performed by the display image determining unit 1801 according to the determination method 2 will be described with reference to the flow chart shown in FIG. 15.

Figure 14:
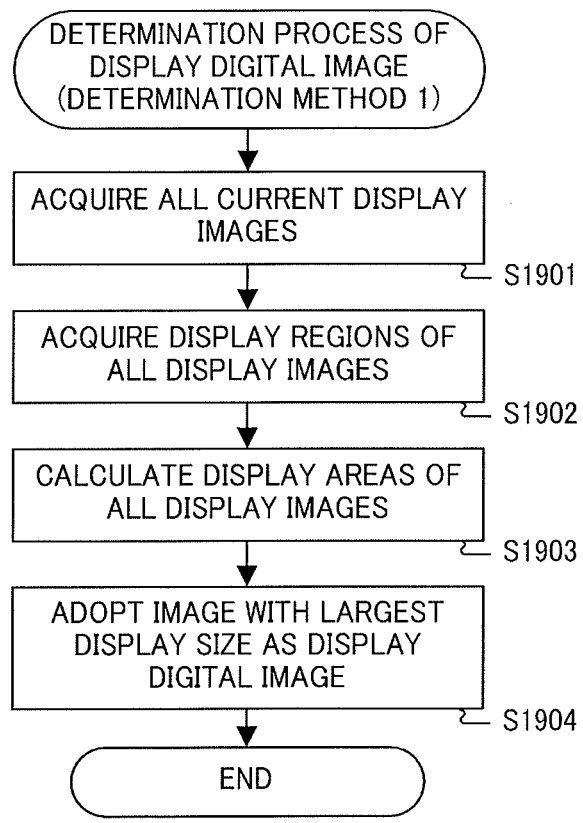
FIG. 14 is a flowchart showing a first determination method for a display digital image according to the third embodiment.

Since processes in steps S2001 and S2002 are the same as the processes in steps S1901 and S1902 in the flowchart shown in FIG. 14, a description thereof will be omitted.

In step S2003, the display image determining unit 1801 of the control device 2 uses the control device communicating unit 207 to transmit a command for inquiring a film placement region to the liquid crystal display device 1.

In step S2004, the display device communicating unit 106 of the liquid crystal display device 1 receives the command and notifies the command to the display device control unit 110.

In step S2005, the display device control unit 110 of the liquid crystal display device 1 receives an inquiry instruction with respect to a film placement region from the display device communicating unit 106 and issues an instruction to the film placement region calculating unit 113 to calculate a film placement region.

Upon receiving the instruction from the display device control unit 110, the film placement region calculating unit 113 of the liquid crystal display device 1 instructs the display device GUI generating unit 102 to create a white display patch to be displayed on the entire display region of the screen. Subsequently, the film placement region calculating unit 113 instructs the scan sensor 114 to scan a front surface of the liquid crystal panel 105. Since a film image has been placed on the screen by the time point where the present process is performed, the film placement region calculating unit 113 is to acquire a scanned image representing a state where the film image is placed on the white display patch displayed on the entire display region of the screen such as shown in FIG. 7A. Subsequently, the film placement region calculating unit 113 analyzes the acquired scanned image and calculates a film placement region (xf, yf, wf, hf) in the screen. Finally, the film placement region calculating unit 113 instructs the display device GUI generating unit 102 to erase the white display patch and returns the calculated region information (xf, yf, wf, hf) of the film placement region to the display device control unit 110.

In step S2006, the display device control unit 110 of the liquid crystal display device 1 uses the display device communicating unit 106 to transmit the region information of the film placement region obtained in step S2005 to the control device 2 as a response to the inquiry instruction with respect to the film placement region. The region information of the film placement region is (xf, yf, wf, hf).

In step S2007, the control device communicating unit 207 of the control device 2 receives the region information (xf, yf, wf, hf) of the film placement region and notifies the region information (xf, yf, wf, hf) of the film placement region to the display image determining unit 1801.

Figure 17B:
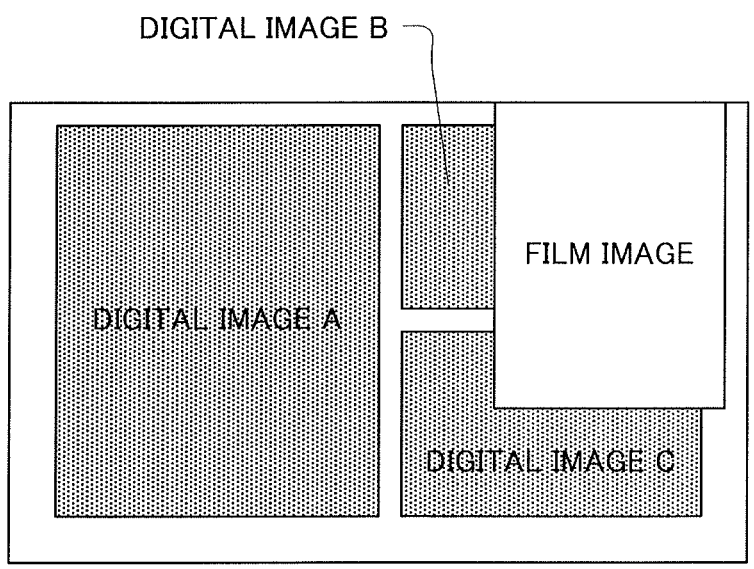

In step S2008, the display image determining unit 1801 of the control device 2 calculates an area of a portion not overlapping with the film image among the respective display regions from the region information of the film placement region and information on the display regions of the digital images A, B, and C. The region information on the film placement region is region information acquired by the control device communicating unit 207. The information on the display regions of the digital images A, B, and C is information acquired in step S2002. The display image determining unit 1801 calculates an area of the gray portion in FIG. 17B among the display regions of the respective digital images.

In step S2009, the display image determining unit 1801 of the control device 2 compares areas of portions not overlapping the film image among the digital images A, B, and C obtained in S2008. In addition, an image having a portion not overlapping the film image with a largest area is determined to be a display digital image. In the present embodiment, the digital image A is determined to be the display digital image. Subsequently, the display image determining unit 1801 hands over the file path of the determined display digital image (in the present embodiment, the digital image A) to the control device control unit 210 and finishes the process.

As a result, an image displayed over a largest area (in the present embodiment, the digital image A) in a region excluding the film placement region among the plurality of digital images displayed in the screen at the start of the divided display mode can be determined to be a display digital image.

<Determination Process of Display Digital Image (Determination Method 3)>

Next, a third determination method (hereinafter, referred to as determination method 3) of a display digital image when a plurality of digital images are being displayed at the start of the divided display mode will be described.

The determination method 3 is a method in which an image displayed at a position that is nearest to a film image among the plurality of digital images displayed in the screen at a time point of start of divided display of an x-ray film illuminator region and an image display region is adopted as a display digital image. This is based on the assumption that, when the user places a film image, the user is highly likely to place the film image close to a digital image which the user wishes to compare the film image with.

A process performed by the display image determining unit 1801 according to the determination method 3 will be described with reference to the flow chart shown in FIG. 16.

Figure 15:
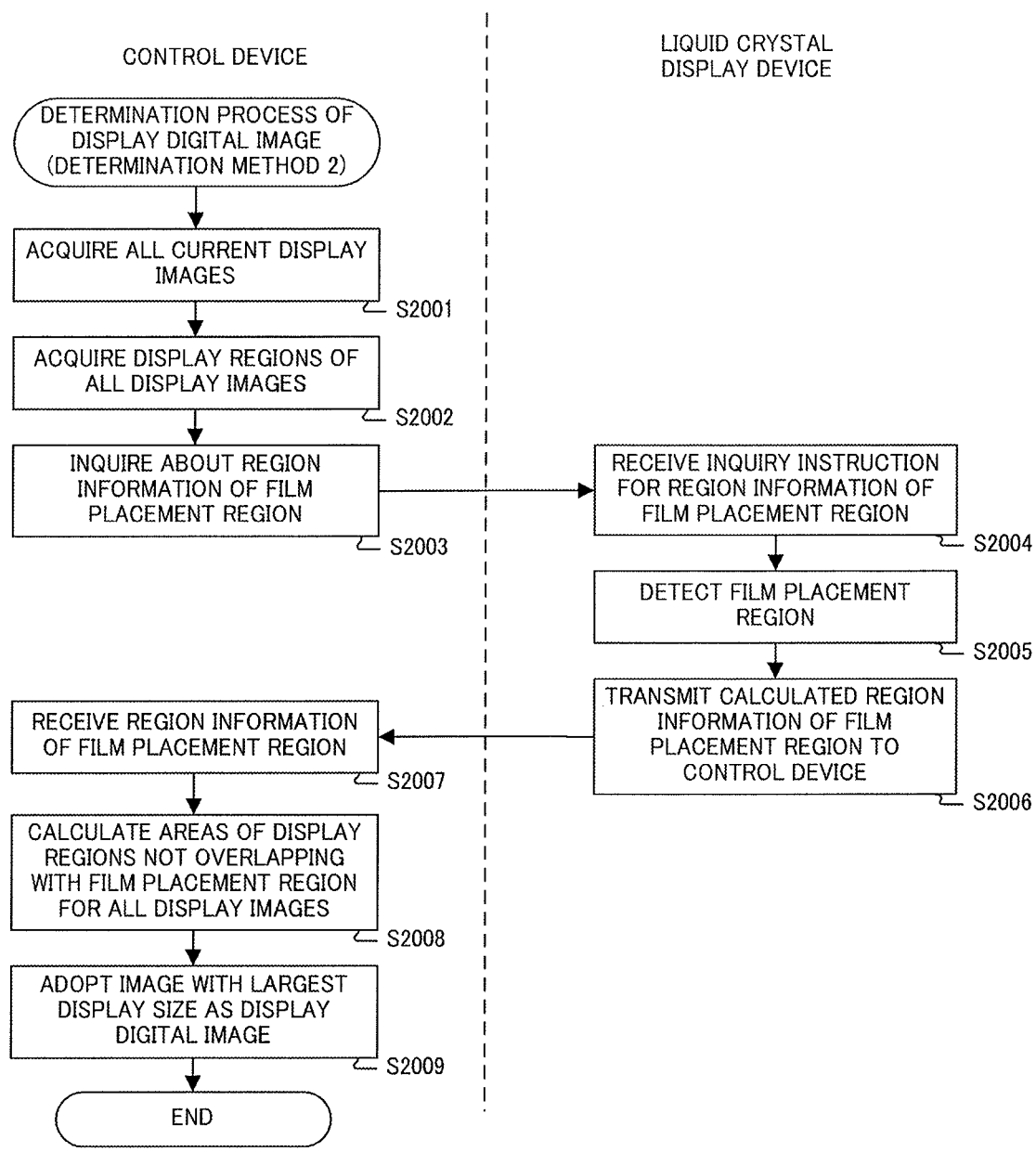
FIG. 15 is a flow chart showing a second determination method for a display digital image according to the third embodiment.
Figure 16:
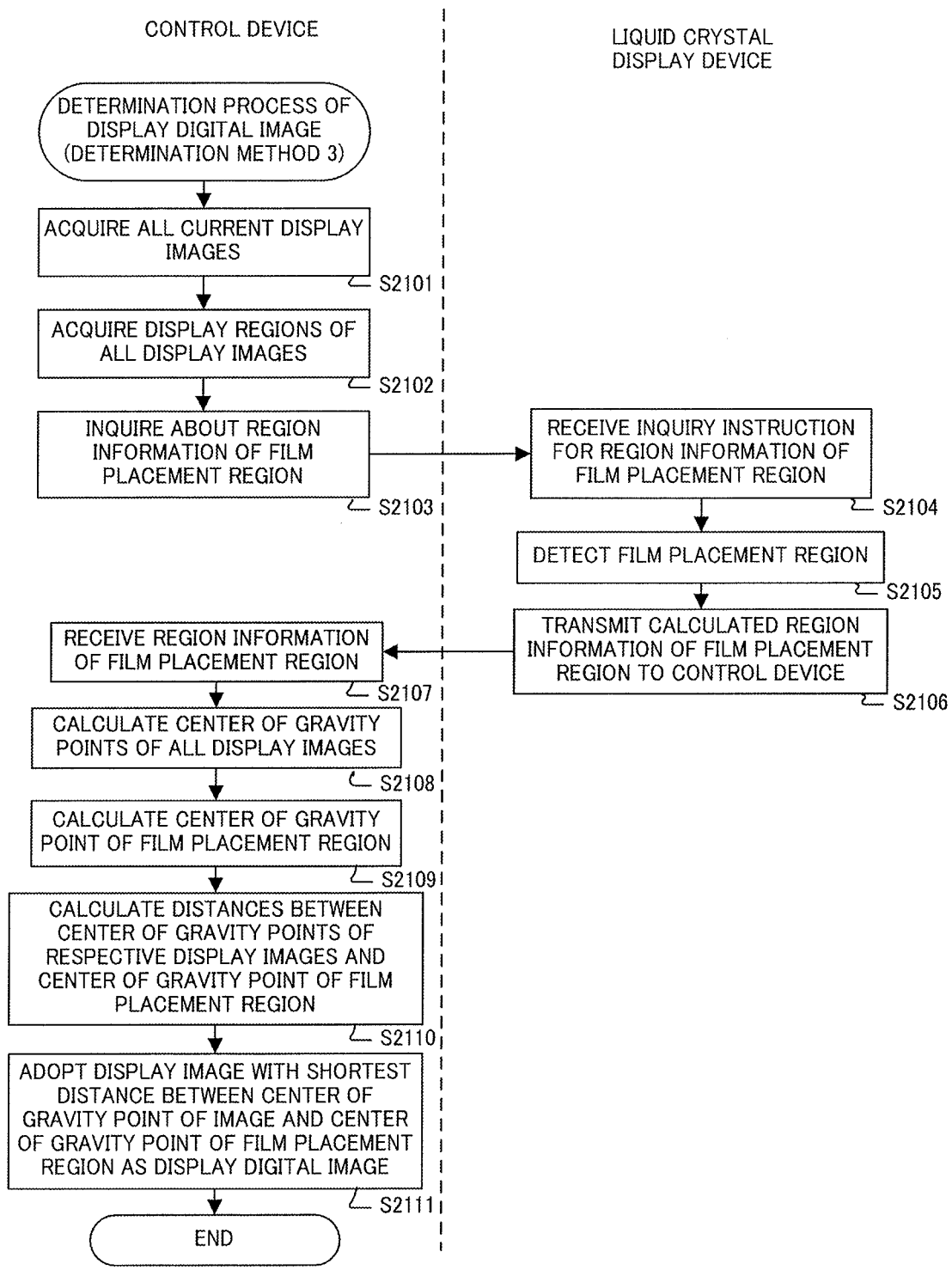
FIG. 16 is a flow chart showing a third determination method for a display digital image according to the third embodiment.

Since processes in steps S2101 to S2107 are the same as the processes in steps S2001 to S2007 in the flow chart shown in FIG. 15, a description thereof will be omitted.

Figure 18B:
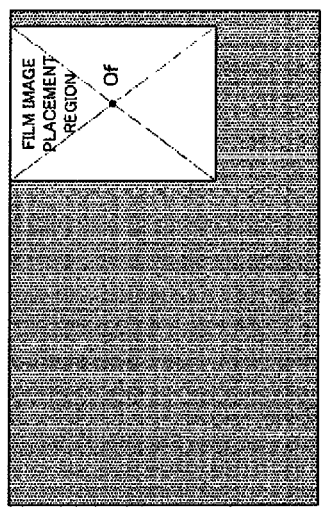
FIGS. 18A to 18C are diagrams showing a positional relationship between a digital image and a film placement region according to the third embodiment.
Figure 18A:
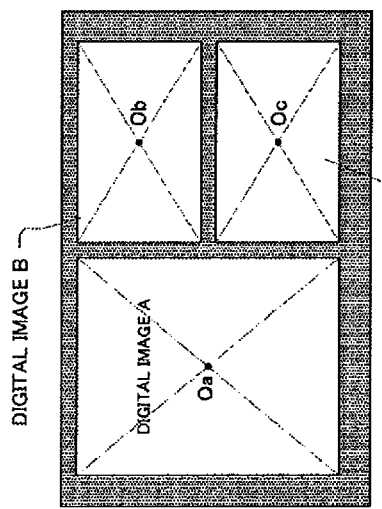

In step S2108, the display image determining unit 1801 of the control device 2 calculates coordinates Oa, Ob, and Oc of center of gravity points that are representative points of the digital images A, B, and C as shown in FIG. 18A from information on the display regions of the respective digital images acquired in step S2102.

In step S2109, the display image determining unit 1801 of the control device 2 calculates coordinates of a center of gravity point Of that is a representative point of a film placement region in the screen as shown in FIG. 18B from the region information (xf, yf, wf, hf) of the film placement region acquired in step S2107.

Figure 18C:
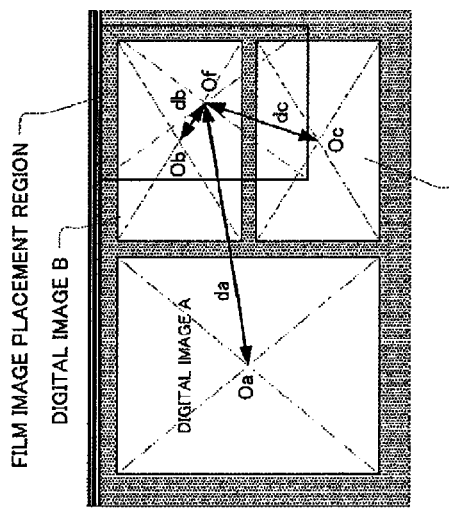

In step S2110, the display image determining unit 1801 of the control device 2 calculates distances from the center of gravity points of the respective digital images to the center of gravity point of the film placement region as shown in FIG. 18C based on the coordinates of the center of gravity points of the respective digital images and the coordinates of the center of gravity point of the film placement region. The center of gravity points of the respective digital images are the center of gravity points Oa, Ob, and Oc of the digital images A, B, and C calculated in step S2108. The center of gravity point of the film placement region is the center of gravity point calculated in step S2109. The distances from the center of gravity points of the respective digital images to the center of gravity point of the film placement region are da, db, and dc.

In step S2111, the display image determining unit 1801 of the control device 2 compares the distances da, db, and dc between the center of gravity points of the digital images A, B, and C and the center of gravity point of the film placement region obtained in step S2110. In addition, the display image determining unit 1801 determines a digital image with a shortest distance between a center of gravity point of a display region of the image and a center of gravity point of the film placement region to be the display digital image. In the present embodiment, since the distance db between the center of gravity point of the digital image B and the center of gravity point of the film placement region is shortest, the digital image B is determined to be the display digital image. Subsequently, the display image determining unit 1801 hands over the file path of the determined display digital image (in the present embodiment, the digital image B) to the control device control unit 210 and finishes the process.

As a result, a digital image displayed at a position that is nearest to the film placement region (in the present embodiment, the digital image B) among the plurality of digital images displayed in the screen at the start of the divided display mode can be determined to be a display digital image.

As described above, three methods of determining a display digital image when a plurality of digital images are being displayed at the start of the divided display mode in the comparative diagnosis system according to the present embodiment have been illustrated. By determining a display digital image conforming to a use case of the user, the user's convenience can be improved.

Moreover, when an image displayed over a largest area exists in plurality at the start of the divided display mode in the determination method 1 according to the third embodiment, a display digital image may be determined by performing any of the determination method 2, the determination method 3, and both determination methods on the plurality of images.

While examples in a comparative diagnosis system constituted by the liquid crystal display device 1, the control device 2, the image signal line 3, and the communication signal line 4 have been presented in the third embodiment described above, a display digital image may be determined by a similar method with the comparative diagnosis device according to the second embodiment.

Fourth Embodiment

In the present embodiment, an example of a comparative diagnosis system capable of performing display by dividing a single screen into two regions including an x-ray film illuminator region and an image display region and a control method thereof will be described in a similar manner to the first embodiment. When a display position of a digital image is determined, the comparative diagnosis system according to the present embodiment determines an x-ray film illuminator region in accordance with the display position of the digital image. In the present embodiment, an x-ray film illuminator region is automatically set at a position where light leakage from the x-ray film illuminator region does not influence the digital image and which is as close to the display position of the digital image as possible.

The present embodiment will be described with a focus on a difference from the first embodiment. The same reference numerals as the first embodiment will be used for portions with the same contents as the first embodiment.

Hereinafter, the present embodiment will be described with reference to the drawings.

In a similar manner to the first embodiment, the comparative diagnosis system according to the present embodiment is constituted by the liquid crystal display device 1, the control device 2, the image signal line 3, and the communication signal line 4 (FIG. 2).

Figure 19:
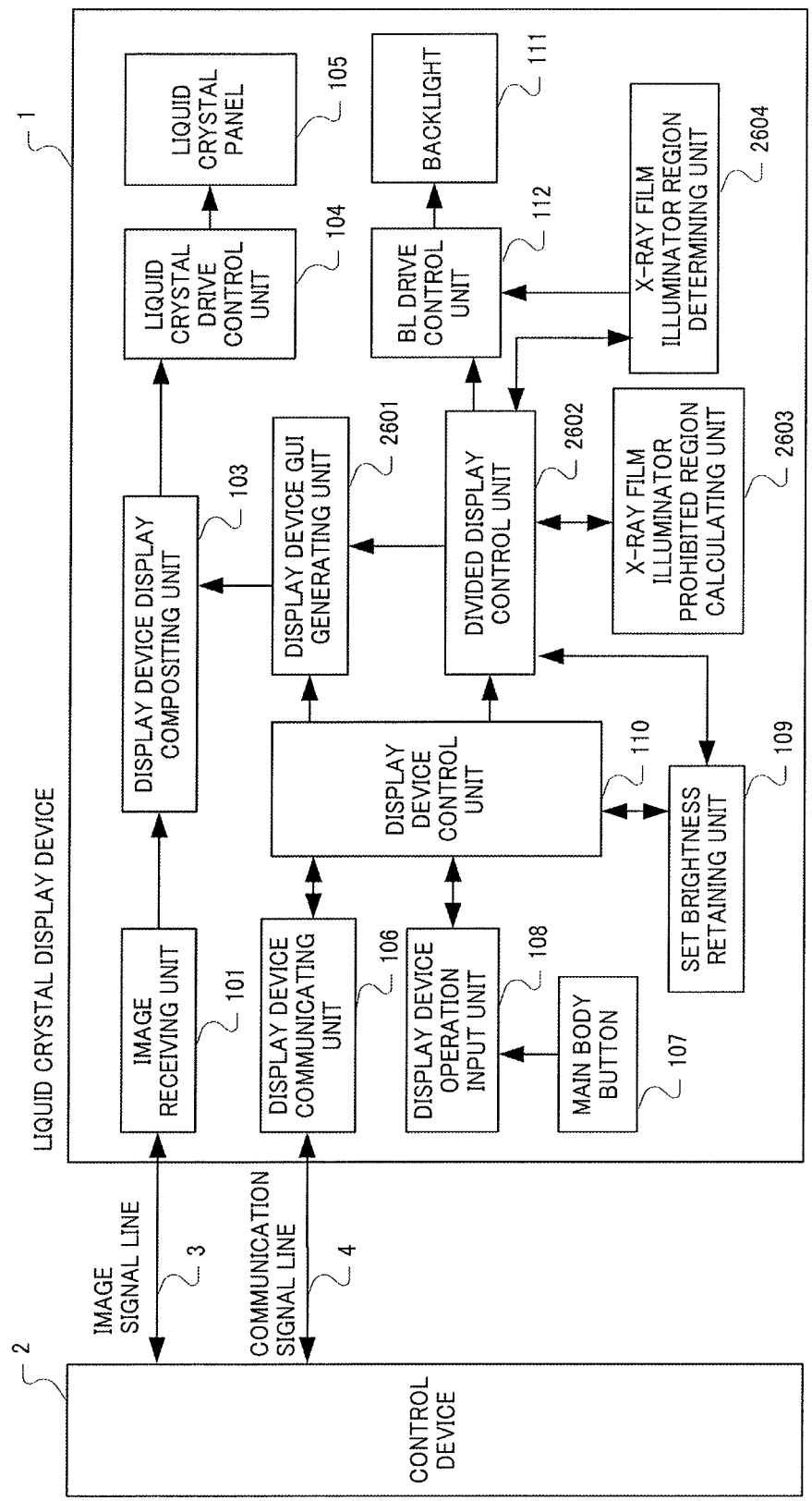
FIG. 19 is a block diagram showing a configuration of a liquid crystal display device according to a fourth embodiment.

Next, differences of functional blocks of the liquid crystal display device 1 according to the present embodiment from the first embodiment will be described with reference to FIG. 19.

A display device GUI generating unit 2601 generates image data for displaying a GUI such as a warning and a message in response to an instruction from the display device control unit 110 and transmits the image data to the display device display compositing unit 103. In addition, the display device GUI generating unit 2601 also receives an instruction to generate a white display patch for an x-ray film illuminator region from a divided display control unit 2602 (to be described later), creates a white display patch in an instructed size, and transmits the white display patch to the display device display compositing unit 103.

Under the control of the display device control unit 110, the divided display control unit 2602 controls the set brightness retaining unit 109, the display device GUI generating unit 2601, an x-ray film illuminator prohibited region calculating unit 2603 and an x-ray film illuminator region determining unit 2604 (to be described later), and a BL drive control unit 112. In addition, the divided display control unit 2602 performs divided display of an x-ray film illuminator region and an image display region. A detailed process will be described in the flows to be presented below.

In response to an instruction from the divided display control unit 2602, the x-ray film illuminator prohibited region calculating unit 2603 calculates an "x-ray film illuminator prohibited region" in the screen of the liquid crystal display device 1. In this case, an x-ray film illuminator prohibited region refers to a region that is not set as an x-ray film illuminator region when setting the x-ray film illuminator region near a digital image in order to perform a comparative diagnosis with the digital image. In the present embodiment, a region combining a digital image display region and a region of a predetermined range around the digital image display region is assumed to be the x-ray film illuminator prohibited region. A region of a predetermined range refers to a region that is not desirably set as an x-ray film illuminator region because, if an x-ray film illuminator region exists within the range, the digital image is influenced by light leakage from the x-ray film illuminator region.

In accordance with an instruction from the divided display control unit 2602, the x-ray film illuminator region determining unit 2604 determines a BL control block to be used as an x-ray film illuminator region and a region in the screen to be used as an x-ray film illuminator region.

Figure 20:
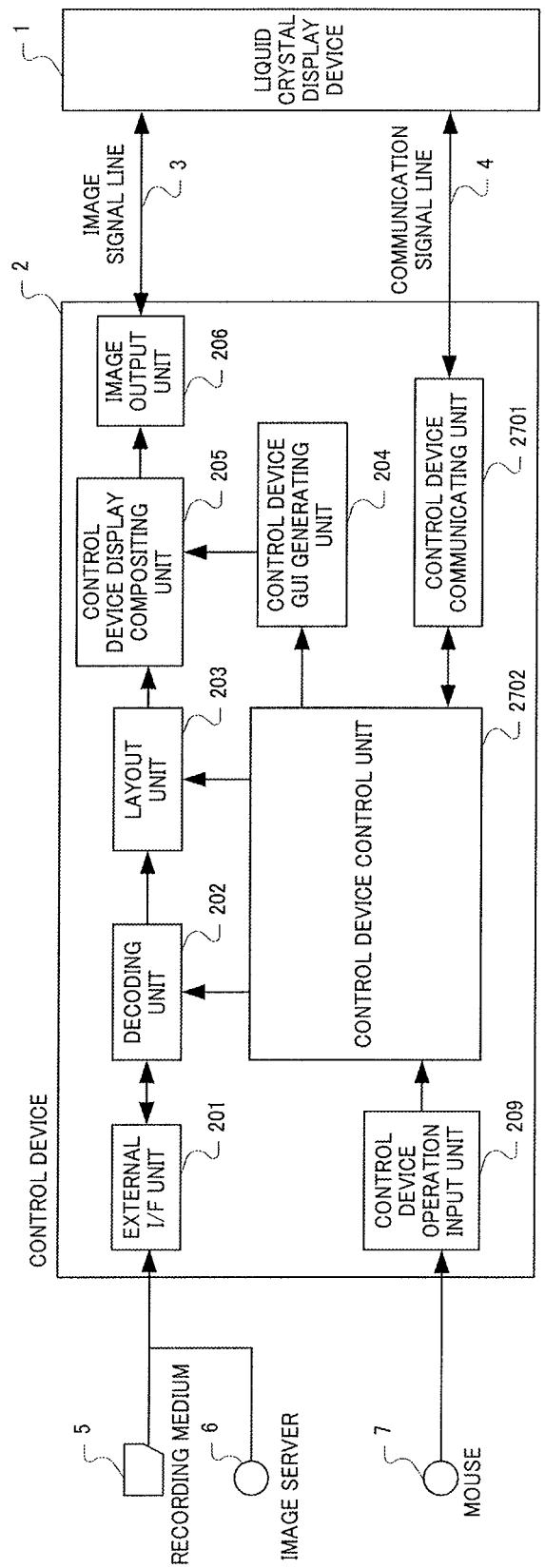
FIG. 20 is a block diagram showing a configuration of a control device according to the fourth embodiment.

Next, differences of functional blocks of the control device 2 according to the present embodiment from the first embodiment will be described with reference to FIG. 20.

A control device communicating unit 2701 creates a communication command in accordance with a command transmission instruction from a control device control unit 2702 (to be described later) and transmits the communication command to the liquid crystal display device 1. In addition, the control device communicating unit 2701 receives a communication command from the liquid crystal display device 1 and analyzes contents of the command. An analysis result is transmitted to the control device control unit 2702. Detailed contents of communication will be described in the flows presented below.

In response to a user operation, the control device control unit 2702 causes the decoding unit 202 to read and decode appropriate digital image data and instructs the layout unit 203 to layout the digital image. Accordingly, a digital image designated by the user is displayed in the screen of the liquid crystal display device 1. In addition, the control device control unit 2702 manages the digital image being displayed. Furthermore, the control device control unit 2702 controls the liquid crystal display device 1 via the control device communicating unit 2701 and performs a process for realizing divided display of an x-ray film illuminator region and an image display region. A detailed process will be described in the flows to be presented below.

Next, a divided display process of the comparative diagnosis system according to the present embodiment will be described with reference to the flow charts shown in FIGS. 21 and 22.

Figure 23C:
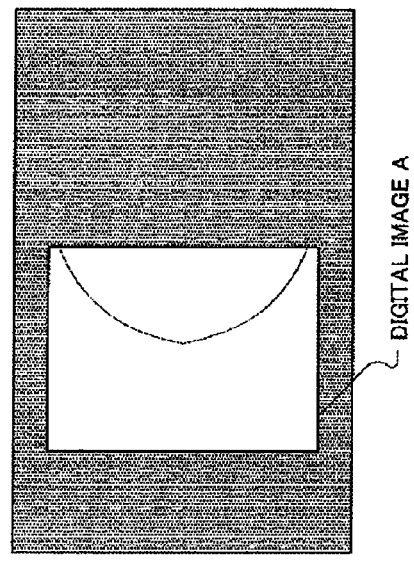
FIGS. 23A to 23D are diagrams showing examples of a display screen and an x-ray film illuminator prohibited region according to the fourth embodiment.
Figure 23D:
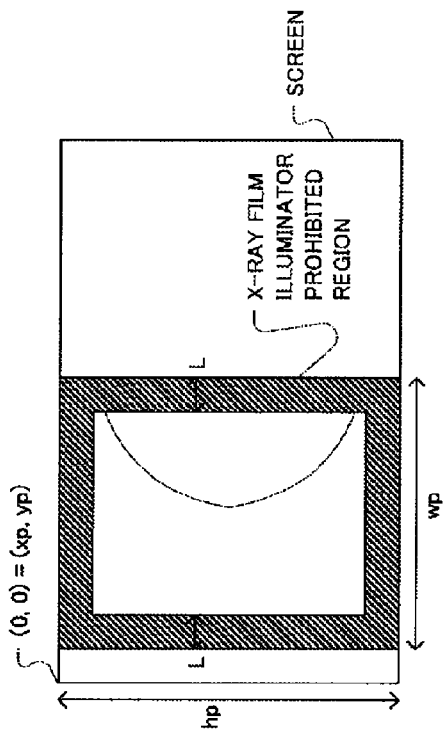
Figure 23A:
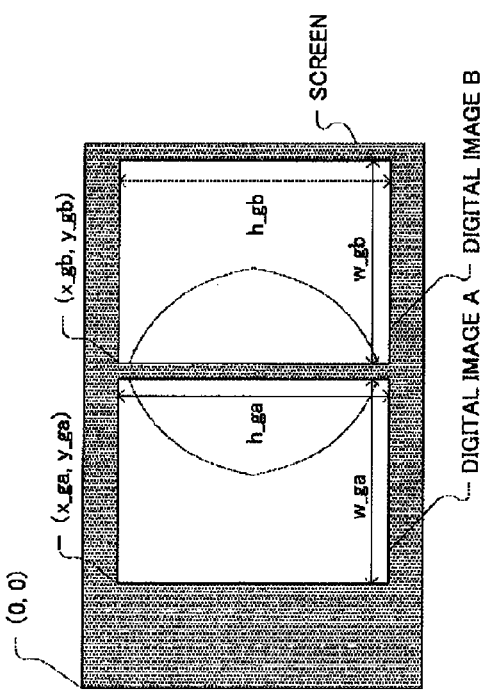

As shown in FIG. 23A, let us assume a state exists where one or more medical digital images read from the recording medium 5 or the image server 6 are displayed in the screen of the liquid crystal display device 1 and is used for diagnosis prior to performing divided display. This display state is realized by processes described below. Specifically, in the control device 2, the control device control unit 2702 uses the decoding unit 202 to decode digital images A and B read from the recording medium 5 or the image server 6. Furthermore, the control device control unit 2702 instructs the layout unit 203 to lay out the image A in region (x_ga, y_ga, w_ga, h_ga) and the image B in region (x_gb, y_gb, w_gb, h_gb).

In a similar manner to the first embodiment, it is assumed that a timing at which the comparative diagnosis system starts divided display is a timing at which the control device 2 causes a GUI (not shown) for setting ON/OFF of divided display to be displayed and the user performs an operation to set divided display=ON on the GUI using the mouse 7.

<Divided Display Control Process>

First, a divided display control process in the comparative diagnosis system according to the present embodiment will be described with reference to the flow chart shown in FIG. 21.

Figure 21:
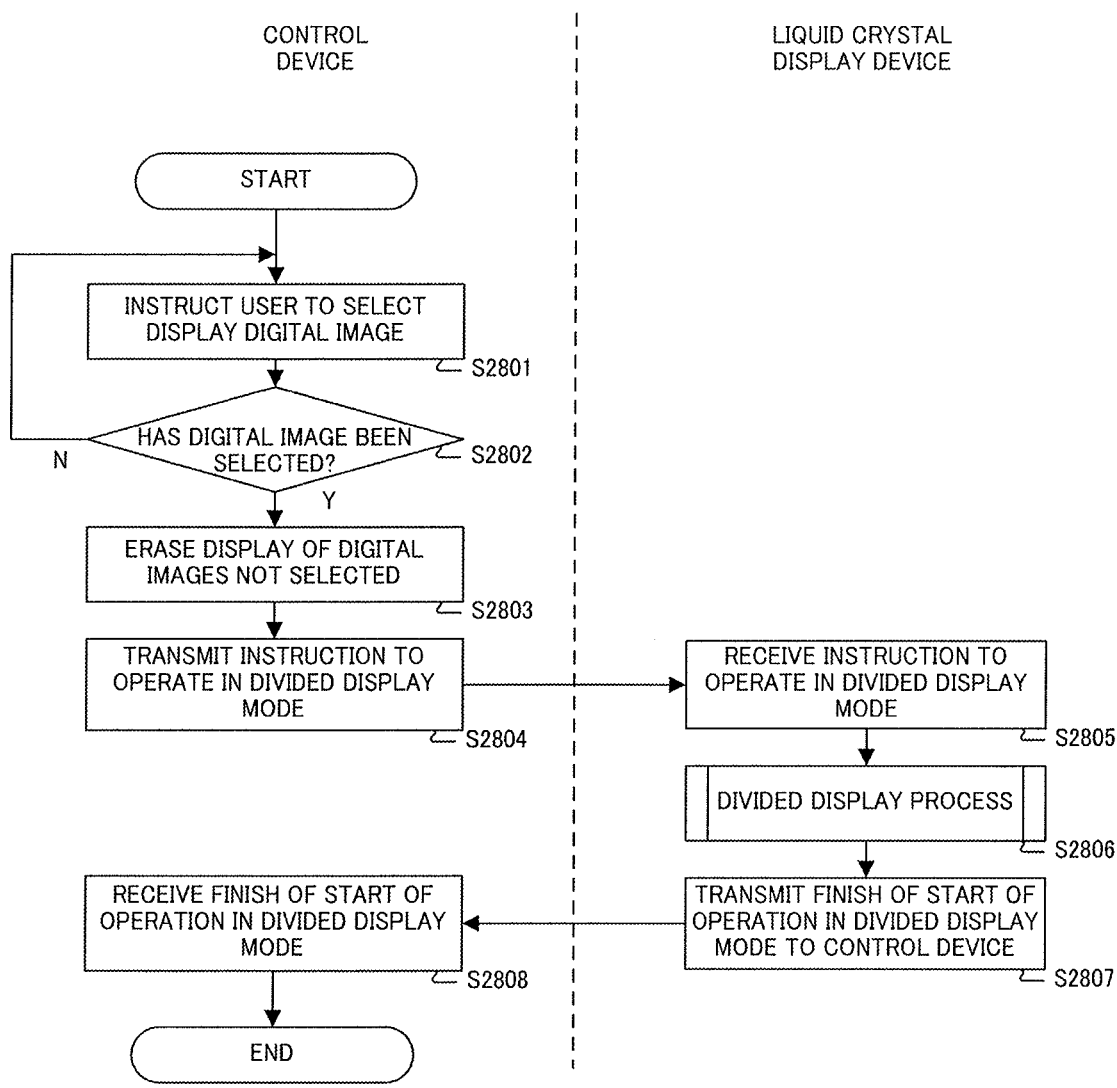
FIG. 21 is a flow chart showing a processing procedure of dividing process control according to the fourth embodiment.

It is assumed that the flow chart shown in FIG. 21 starts at a time point where, in a state in which only a digital image is displayed in the screen such as shown in FIG. 23A, the control device control unit 2702 of the control device 2 detects that divided display=ON has been set by a user operation using the mouse 7.

Figure 23B:
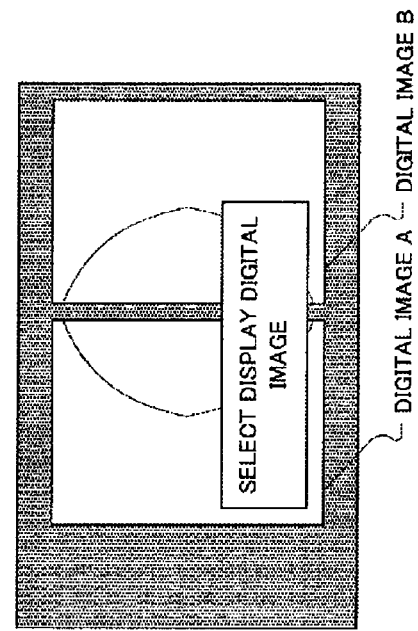

In step S2801, the control device control unit 2702 of the control device 2 instructs the control device GUI generating unit 204 to generate a GUI for prompting selection of a digital image to be used for a comparative diagnosis with a film image among the plurality of digital images that are being displayed. As a result of this process, a GUI such as that shown in FIG. 23B is displayed on the screen (the liquid crystal panel 105) of the liquid crystal display device 1.

In step S2802, the control device control unit 2702 of the control device 2 determines whether or not a digital image to be used for a comparative diagnosis (hereinafter, referred to as a diagnostic digital image) has been selected. In the present embodiment, the control device control unit 2702 makes this determination based on whether the digital image A or the digital image B in the screen has been clicked by the mouse 7 when the GUI shown in FIG. 23B is being displayed. When clicked, the control device control unit 2702 determines that a diagnostic digital image has been selected and advances the process to step S2803 after erasing the GUI. When not clicked, the control device control unit 2702 determines that a diagnostic digital image has not been selected and returns the process to step S2801. In the present embodiment, it is assumed that the digital image A has been selected.

In step S2803, the control device control unit 2702 of the control device 2 instructs the layout unit 203 to erase digital images (the digital image B) other than the selected diagnostic digital image. In response to the instruction from the control device control unit 2702, the layout unit 203 of the control device 2 displays only the digital image A that is the diagnostic digital image and erases the digital image B as shown in FIG. 23C by filling in the display region of the digital image B with a same color as the background.

In step S2804, the control device control unit 2702 of the control device 2 uses the control device communicating unit 2701 to transmit a command to cause the liquid crystal display device 1 to start operation in the divided display mode together with region information of the diagnostic digital image. In this case, the diagnostic digital image is the digital image A and the region information is (x_ga, y_ga, w_ga, h_ga).

In step S2805, the display device communicating unit 106 of the liquid crystal display device 1 receives the command and notifies the command to the display device control unit 110.

In step S2806, the display device control unit 110 of the liquid crystal display device 1 receives the instruction and hands over the received region information of the diagnostic digital image (the digital image A) to the divided display control unit 2602. At the same time, the display device control unit 110 issues an instruction to the divided display control unit 2602 to operate in a divided display mode of an x-ray film illuminator region and an image display region.

In response to the instruction, the divided display control unit 2602 of the liquid crystal display device 1 performs a process for realizing divided display. A detailed process will be described in the flow titled <Divided display process> to be presented below.

In step S2807, the display device control unit 110 of the liquid crystal display device 1 uses the display device communicating unit 106 to transmit a message informing that start of operation in the divided display mode has finished to the control device 2.

In step S2808, the control device communicating unit 2701 of the control device 2 receives the message informing that start of operation in the divided display mode has finished and notifies the message to the control device control unit 2702.

The control device control unit 2702 of the control device 2 receives the message informing finish of operation of the liquid crystal display device 1 in the divided display mode from the control device communicating unit 2701 and concludes the present process.

<Divided Display Process>

Next, a divided display process will be described with reference to the flow chart shown in FIG. 22.

Figure 22:
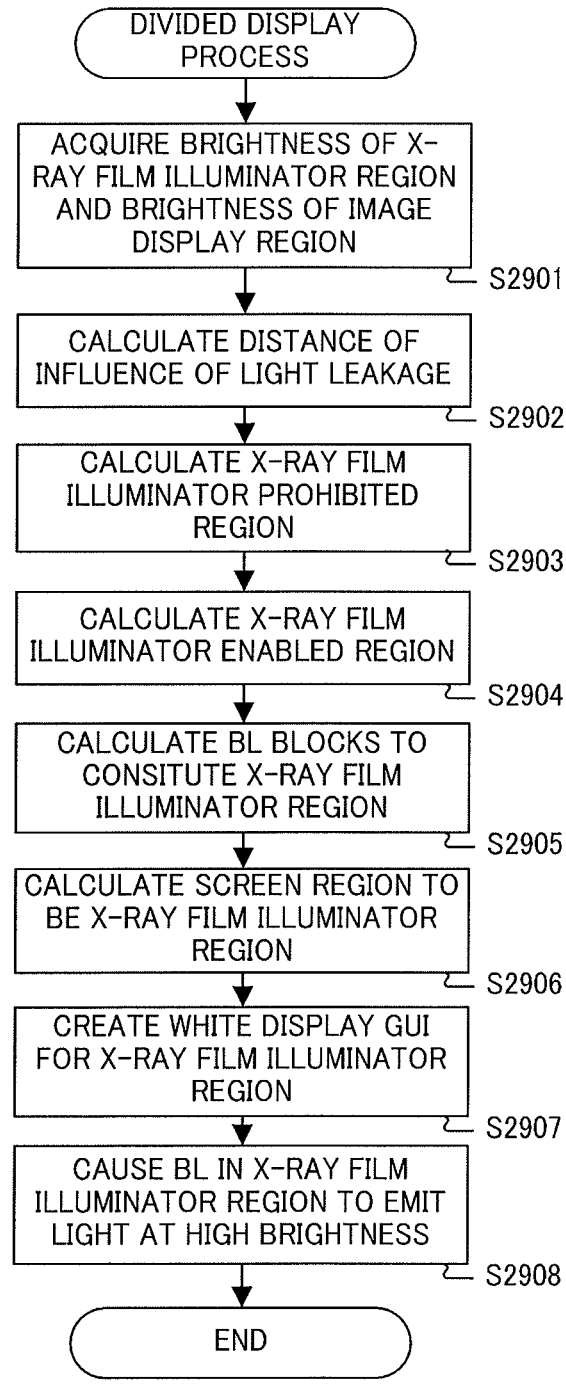
FIG. 22 is a flow chart showing a processing procedure of divided display according to the fourth embodiment.

The flow chart shown in FIG. 22 represents details of the process performed in step S2806 in the flow chart shown in FIG. 21. It is assumed that the process is executed upon the divided display control unit 2602 of the liquid crystal display device 1 receiving a divided display instruction from the display device control unit 110 together with region information of a diagnostic digital image. In this case, the diagnostic digital image is the digital image A and the region information is (x_ga, y_ga, w_ga, h_ga).

In step S2901, the divided display control unit 2602 of the liquid crystal display device 1 acquires information on a set brightness of the x-ray film illuminator region and a set brightness of the image display region from the set brightness retaining unit 109.

In step S2902, the divided display control unit 2602 of the liquid crystal display device 1 hands over the region information of the diagnostic digital image and the information on the set brightness of the x-ray film illuminator region and the set brightness of the image display region to the x-ray film illuminator prohibited region calculating unit 2603. In addition, the divided display control unit 2602 instructs the x-ray film illuminator prohibited region calculating unit 2603 to calculate an x-ray film illuminator prohibited region. In this case, the diagnostic digital image is the digital image A and the region information is (x_ga, y_ga, w_ga, h_ga). The information on the set brightness of the x-ray film illuminator region and the set brightness of the image display region is information acquired in step S2901.

Upon receiving the instruction from the divided display control unit 2602, the x-ray film illuminator prohibited region calculating unit 2603 of the liquid crystal display device 1 calculates a distance of influence L [pixels] of light leakage from the x-ray film illuminator region to the image display region. The x-ray film illuminator prohibited region calculating unit 2603 retains a light leakage table such as that shown in FIG. 8 in a similar manner to the display prohibited region calculating unit 116 according to the first embodiment. For example, if the set brightness acquired in step S2901 of the x-ray film illuminator region is 2000 cd/m$^2$ and the set brightness acquired in step S2901 of the image display region is 500 cd/m$^2$, then there is a difference in brightness of 1500 cd/m$^2$. In this case, a light leakage influence distance L of 300 pixels is obtained from the light leakage table shown in FIG. 8.

In step S2903, the x-ray film illuminator prohibited region calculating unit 2603 of the liquid crystal display device 1 calculates an x-ray film illuminator prohibited region based on the region information on the diagnostic digital image handed over from the divided display control unit 2602 and on the light leakage influence distance L. In this case, the region information of the diagnostic digital image is (x_ga, y_ga, w_ga, h_ga). The light leakage influence distance L is the distance L acquired in step S2902. An x-ray film illuminator prohibited region refers to a region which is a display region of a digital image and therefore cannot be set as an x-ray film illuminator region and which is not desirably set as an x-ray film illuminator region due to a display brightness of the digital image being influenced by light leakage from the x-ray film illuminator region. The x-ray film illuminator prohibited region according to the present embodiment is a region (xp, yp, wp, hp) created by adding the light leakage influence distance L to the periphery of a display region (x_ga, y_ga, w_ga, h_ga) of the diagnostic digital image (the digital image A) as shown in FIG. 23D. Finally, the x-ray film illuminator prohibited region calculating unit 2603 returns the obtained region information (xp, yp, wp, hp) of the x-ray film illuminator prohibited region to the divided display control unit 2602.

In step S2904, the divided display control unit 2602 of the liquid crystal display device 1 issues an instruction to the x-ray film illuminator region determining unit 2604 to determine an x-ray film illuminator region in the screen of the liquid crystal display device 1 together with the region information (xp, yp, wp, hp) of the x-ray film illuminator prohibited region.

The x-ray film illuminator region determining unit 2604 of the liquid crystal display device 1 receives the region information (xp, yp, wp, hp) of the x-ray film illuminator prohibited region from the divided display control unit 2602 and starts a process for determining the x-ray film illuminator region (xs, ys, ws, hs).

Figure 24A:
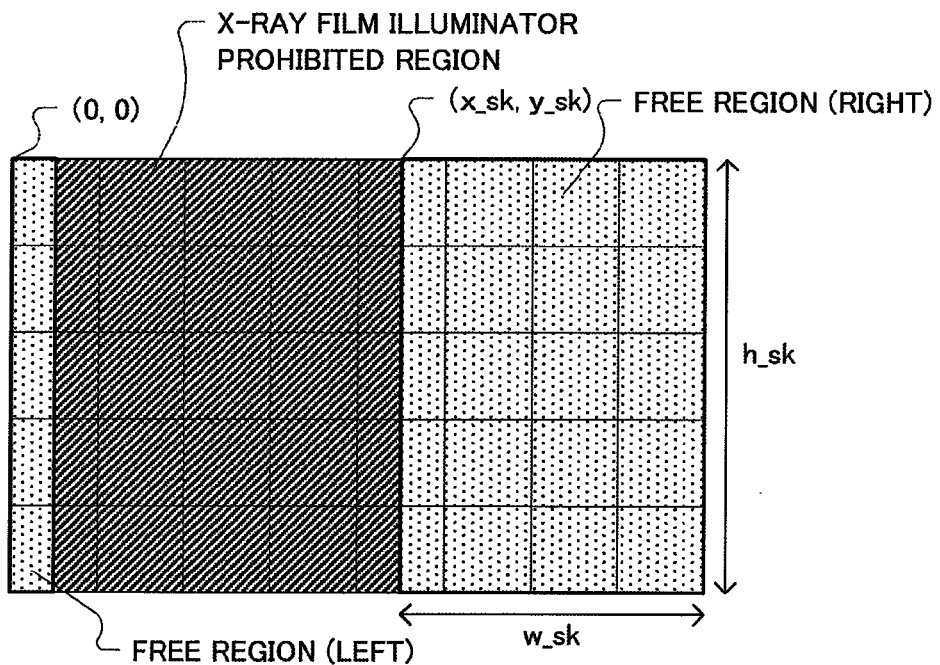
FIGS. 24A and 24B show examples of a free region and an x-ray film illuminator region BL control block according to the fourth embodiment.

In step S2904, the x-ray film illuminator region determining unit 2604 of the liquid crystal display device 1 calculates a region that can be allocated as an x-ray film illuminator region (hereinafter, referred to as an x-ray film illuminator enabled region). When calculating an x-ray film illuminator enabled region, the x-ray film illuminator region determining unit 2604 first calculates a free region that is a region obtained by subtracting an x-ray film illuminator prohibited region from an entire display region of the screen. In the present embodiment, a region adjacent to the left and a region adjacent to the right of an x-ray film illuminator prohibited region (xp, yp, wp, hp) are extracted as free regions. When the x-ray film illuminator prohibited region is as shown in FIG. 23D, a free region (right) and a free region (left) are extracted as free regions as shown in FIG. 24A. Next, the x-ray film illuminator region determining unit 2604 determines a region with a greater area between the extracted right free region and the extracted left free region as the x-ray film illuminator enabled region. In the example shown in FIG. 24A, since an area of the right free region is larger than that of the left free region, the right free region is determined to be the x-ray film illuminator enabled region (x_sk, y_sk, w_sk, h_sk).

Figure 24B:
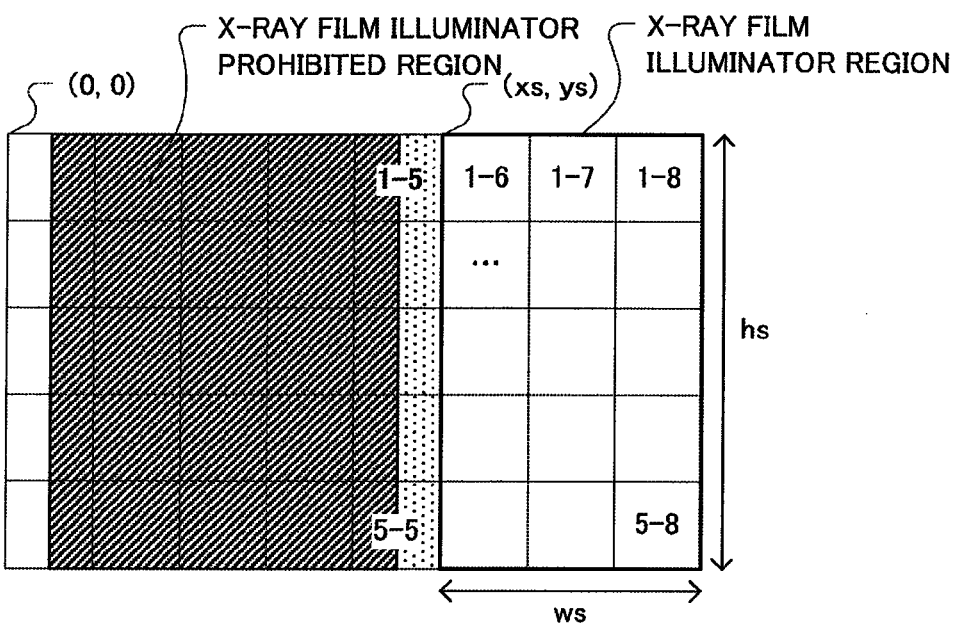

In step S2905, the x-ray film illuminator region determining unit 2604 of the liquid crystal display device determines an x-ray film illuminator region. Specifically, the x-ray film illuminator region determining unit 2604 determines BL control blocks to constitute an x-ray film illuminator region (x-ray film illuminator region BL control blocks). In this case, x-ray film illuminator region BL control blocks are assumed to be BL control blocks that entirely belong to the x-ray film illuminator enabled region. In the example shown in FIG. 24A, 15 BL control blocks 1-6 to 5-8 that entirely belong to the x-ray film illuminator enabled region (the free region (right)) as shown in FIG. 24B are assumed to be x-ray film illuminator region BL control blocks. Subsequently, the x-ray film illuminator region determining unit 2604 saves information (BL control block numbers) on the x-ray film illuminator region BL control blocks obtained above.

In step S2906, the x-ray film illuminator region determining unit 2604 calculates region information of the x-ray film illuminator region on the entire screen based on layout information of BL control blocks of the backlight 111 that is retained in advance and on the information regarding the x-ray film illuminator region BL control blocks. In addition, the x-ray film illuminator region determining unit 2604 returns the calculated region information (xs, ys, ws, hs) of the x-ray film illuminator region to the divided display control unit 2602. The x-ray film illuminator region on the entire screen is the region depicted by a portion framed by a bold line in FIG. 24B. The layout information of the BL control blocks is as shown in FIG. 2. The information regarding the x-ray film illuminator region BL control blocks is the information acquired in step S2905.

Figure 25A:
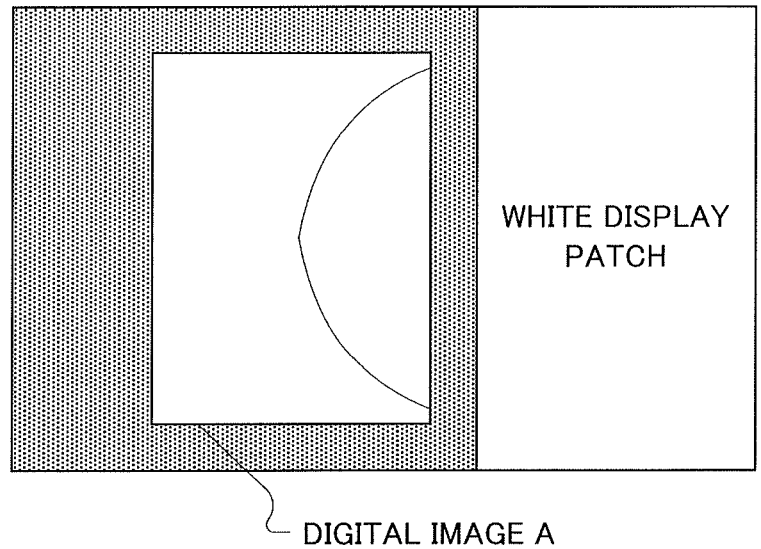
FIGS. 25A and 25B show a display image after a divided display process and a state where a film image is placed according to the fourth embodiment.

In step S2907, the divided display control unit 2602 of the liquid crystal display device 1 hands over the region information (xs, ys, ws, hs) of the x-ray film illuminator region acquired in step S2906 to the display device GUI generating unit 2601. In addition, the divided display control unit 2602 instructs the display device GUI generating unit 2601 to display a white display patch for an x-ray film illuminator in the x-ray film illuminator region. The display device GUI generating unit 2601 sends the white display patch created in adherence to the instruction to the display device display compositing unit 103 and the white display patch is displayed on the liquid crystal panel 105. In step S2803 of the <divided display control process> (FIG. 21), the display device display compositing unit 103 composites the image created by the control device 2 (FIG. 23C) and the white display patch created in the present process. Accordingly, an image in which the diagnostic digital image and the white display patch are arranged side by side is displayed as shown in FIG. 25A.

In step S2908, the divided display control unit 2602 of the liquid crystal display device 1 hands over the set brightness of the x-ray film illuminator region and the set brightness of the image display region acquired in step S2901 to the BL drive control unit 112 and instructs the BL drive control unit 112 to adjust brightness of each BL control block.

Upon receiving the instruction, the BL drive control unit 112 of the liquid crystal display device 1 acquires information on the x-ray film illuminator region BL control blocks obtained in step S2905 from the x-ray film illuminator region determining unit 2604. In addition, the BL drive control unit 112 causes the x-ray film illuminator region BL control blocks to emit light at the set brightness of the x-ray film illuminator region and the BL control blocks belonging to regions other than the x-ray film illuminator to emit light at the set brightness of the image display region. According to the process described above, divided display of the x-ray film illuminator region and the image display region is realized and an operation in the divided display mode is started by the liquid crystal display device 1.

Figure 25B:
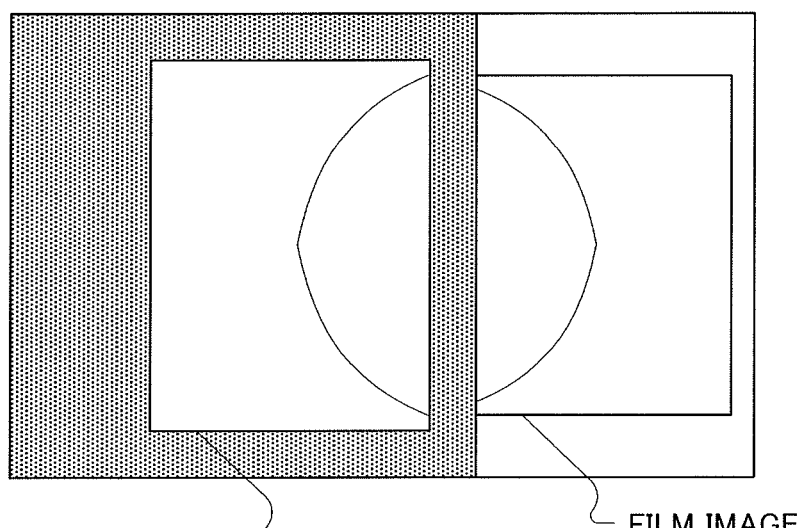

After finish of start of operation in the divided display mode, when placing a film image on the screen of the liquid crystal display device 1, the user can place the film image at a position that is adjacent to a diagnostic digital image as shown in FIG. 25B. Therefore, a comparative diagnosis of the digital image and the film image can be readily performed.

As described above, with the comparative diagnosis system according to the present embodiment, when performing comparative diagnosis by arranging and displaying a digital image and a film image in a single screen, an x-ray film illuminator region is automatically set at a position as close to the digital image as possible in accordance with a display position of the digital image. Therefore, since a user operation for manually moving a display position of the digital image to a position adjacent to the x-ray film illuminator region is no longer required, the digital image and the film image can be arranged side by side for observation in an efficient manner. As a result, convenience is improved.

In addition, when the comparative diagnosis device according to the present embodiment sets an x-ray film illuminator region, since the x-ray film illuminator region is set to a region where light leakage from the x-ray film illuminator region does not influence a display region of a digital image, the digital image can be accurately displayed.

Moreover, in the fourth embodiment described above, an example has been presented in which, when determining a diagnostic digital image, a selection of a digital image is made by the user by a click operation from digital images displayed in advance. Alternatively, a GUI (not shown) that prompts the user to select a digital image may be displayed, whereby the digital image selected by the user on the GUI may be displayed as a diagnostic digital image.

In addition, while an example of realization by a comparative diagnosis system constituted by the liquid crystal display device 1, the control device 2, the image signal line 3, and the communication signal line 4 has been presented in the fourth embodiment described above, the fourth embodiment may alternatively be solely realized by a comparative diagnosis device as is the case of the second embodiment.

Moreover, while a mode in which a first region (high brightness region) in a screen is used as an illuminated region (an x-ray film illuminator) and a second region (low brightness region) in the screen is used for image display has been described in the respective embodiments above, the present invention can also be applied to an image display device in an opposite use mode. In other words, the present invention can also be applied to an image display device in a mode in which the second region (the low brightness region) in a screen is used as an illuminated region (an x-ray film illuminator) and the first region (the high brightness region) in the screen is used for image display.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-163511, filed on Aug. 6, 2013, which is hereby incorporated by reference herein in its entirety.

What is claimed is:

1. An image display device comprising:
a light-emitting unit that includes a plurality of light-emitting blocks and is capable of individually controlling an emission brightness of each of the plurality of light-emitting blocks;
a display unit that displays an image on a screen; and
a control unit configured to set an arrangement of a first region in the screen in which a predetermined image is displayed and an arrangement of a second region in the screen which excludes the first region, wherein
an emission brightness of the light-emitting blocks corresponding to the first region is a predetermined brightness,
an emission brightness of the light-emitting blocks corresponding to the second region is a brightness lower than the predetermined brightness, and
the control unit sets the arrangement of the second region on the basis of an influence of light leakage from the light-emitting blocks corresponding to the first region.

2. The image display device according to claim 1, wherein the predetermined brightness is brightness assumed to be used as lighting when observing through an observation object that is placed in front of the first region of the display unit.

3. The image display device according to claim 1, wherein the control unit does not set the second region in a predetermined region which surrounds the first region and in which the influence of light leakage from the light-emitting blocks corresponding to the first region exceeds a predetermined level.

4. The image display device according to claim 3, wherein in a case where there are a plurality of regions excluding the first region and the predetermined region in the screen, the control unit sets the arrangement of the second region in a region having a largest area among the plurality of regions.

5. The image display device according to claim 1, further comprising
an acquiring unit configured to acquire position information relating to a placement region in the screen, in front of which an observation object is placed, wherein
the control unit sets the arrangement of the first region on the basis of the position information acquired by the acquiring unit.

6. The image display device according to claim 5, wherein
the screen is constituted by a plurality of divided regions corresponding to the plurality of light-emitting blocks, and
the control unit sets the arrangement of the first region such that the first region is constituted by a divided region having a portion shared with the placement region.

7. The image display device according to claim 5, wherein the acquiring unit acquires, from an image scanner that scans a display surface of the display unit and generates a scanned image, a scanned image obtained by scanning the display surface in a state where an observation object is placed on the display surface, and analyzes the scanned image to acquire a position of the placement region.

8. The image display device according to claim 5, wherein the display unit includes a touch panel that accepts a touch operation by a user, and
the acquiring unit acquires a position of the placement region on the basis of a touch operation for designating a position of the observation object.

9. The image display device according to claim 1, wherein the control unit is capable of switching between an image display mode in which only the second region is included in the screen and a divided display mode in which the second region and the first region are included in the screen, wherein in a case where the control unit switches the display mode from the image display mode to the divided display mode, the control unit displays a display image, which is an image in accordance with an image that had been displayed in the image display mode, in the second region.

10. The image display device according to claim 9, wherein the display image is the image that had been displayed in the image display mode.

11. The image display device according to claim 9, wherein in a case where a plurality of images have been displayed in the image display mode, the display image is an image selected by a user among the plurality of images.

12. The image display device according to claim 9, wherein in a case where a plurality of images have been displayed in the image display mode, the display image is an image having a largest display area among the plurality of images.

13. The image display device according to claim 9, further comprising
an acquiring unit configured to acquire position information relating to a placement region in the screen front of which an observation object is placed, wherein
in a case where a plurality of images have been displayed in the image display mode, the display image is an image, of which an area of a part other than a part overlapping the placement region is largest among the plurality of images.

14. The image display device according to claim 9, further comprising
an acquiring unit configured to acquire position information relating to a placement region in the screen, in front of which an observation object is placed, wherein
in a case where a plurality of images have been displayed in the image display mode, the display image is an image, of which a distance from representative point to a representative point of the placement region is nearest among the plurality of images.

15. The image display device according to claim 1, wherein the control unit is further configured:
to set an arrangement of a third region which is around the first region and in which the predetermined image is not displayed,
to calculate at least one of a size and a position of the third region on the basis of information related to the influence of light leakage from the light-emitting blocks corresponding to the first region, and
to set an arrangement of the second region in a region adjacent to the third region.

16. The image display device according to claim 1, wherein an image displayed in the second region is a medical image.

17. The image display device according to claim the first region is a region which is used for lighting a film that is placed in front of the region so that the film is observed by the transmitted light through the film.

18. The image display device according to claim 1, wherein an image displayed in the first region is a white image.

19. The image display device according to claim 1, wherein the control unit is further configured:
to set arrangement of a third region which is around the first region and in which the predetermined image is not displayed, and
to set an arrangement of the second region in a region adjacent to the third region.

20. An image display device comprising:
a light-emitting unit that includes a plurality of light-emitting blocks and is capable of individually controlling an emission brightness of each of the plurality of light-emitting blocks;
a display unit that displays an image on a screen; and
a control unit configured to set an arrangement of a first region in the screen in which a predetermined image is displayed and an arrangement of a second region in the screen which excludes the first region, wherein
an emission brightness of the light-emitting blocks corresponding to the first region is a predetermined brightness,
an emission brightness of the light-emitting blocks corresponding to the second region is brightness lower than the predetermined brightness, and
the control unit sets the arrangement of the first region on the basis of an influence of light leakage from the light-emitting blocks corresponding to the first region.

21. The image display device according to claim 20, wherein the predetermined brightness is brightness assumed to be used as lighting when observing through an observation object that is placed in front of the first region of the display unit.

22. The image display device according to claim 20, wherein the control unit does not set the first region in a predetermined region which surrounds the second region, the predetermined region being such a region that if the first region is in the predetermined region, the influence of light leakage in the second region from the light-emitting blocks corresponding to the first region exceeds a predetermined level.

23. The image display device according to claim 22, wherein in a case where there are a plurality of regions excluding the second region and the predetermined region in the screen, the control unit sets the arrangement of the first region in a region having a largest area among the plurality of regions.

24. The image display device according to claim 20, wherein
the screen is constituted by a plurality of divided regions corresponding to the plurality of light-emitting blocks, and
the control unit sets the arrangement of the first region such that the first region is constituted by a divided region included in a region excluding the second region and the predetermined region in the screen.

25. The image display device according to claim 20, wherein the control unit is further configured:
to set an arrangement of a third region which is around the second region and in which the predetermined image is not displayed,
to calculate at least one of a size and a position of the third region on the basis of information related to the influence of light leakage from the light-emitting blocks corresponding to the first region, and
to set an arrangement of the first region in a region adjacent to the third region.

26. The image display device according to claim 20, wherein an image displayed in the second region is a medical image.

27. The image display device according to claim 20, wherein the first region is a region which is used for lighting a film that is placed in front of the region so that the film is observed by the transmitted light through the film.

28. The image display device according to claim 20, wherein an image displayed in the first region is a white image.

29. The image display device according to claim 20, wherein the control unit is further configured:
to set an arrangement of a third region which is around the second region and in which the predetermined image is not displayed, and
to set an arrangement of the first region in a region adjacent to the third region.

30. A control method for an image display device including:
a light-emitting unit that includes a plurality of light-emitting blocks; and
a display unit that displays an image on a screen,
the control method comprising:
individually controlling an emission brightness of each of the plurality of light-emitting blocks; and
implementing control of setting an arrangement of a first region in the screen in which a predetermined image is displayed and an arrangement of a second region in the screen which excludes the first region, wherein
an emission brightness of the light-emitting blocks corresponding to the first region is a predetermined brightness,
an emission brightness of the light-emitting blocks corresponding to the second region is a brightness lower than the predetermined brightness, and the control includes setting the arrangement of the second region on the basis of an influence of light leakage from the light-emitting blocks corresponding to the first region.

\* \* \* \* \*